(12) United States Patent
Kim et al.

(10) Patent No.: US 9,448,173 B2
(45) Date of Patent: Sep. 20, 2016

(54) DYE-CONJUGATED DENDRIMERS

(75) Inventors: Younghoon Kim, Champaign, IL (US); Sung Hoon Kim, Champaign, IL (US); Melikhan Tanyeri, Champaign, IL (US); John A. Katzenellenbogen, Urbana, IL (US); Charles M. Schroeder, III, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1204 days.

(21) Appl. No.: 13/385,828

(22) Filed: Mar. 8, 2012

(65) Prior Publication Data

US 2012/0256102 A1   Oct. 11, 2012

Related U.S. Application Data

(60) Provisional application No. 61/450,509, filed on Mar. 8, 2011.

(51) Int. Cl.
*G01N 33/58* (2006.01)
*G01N 21/64* (2006.01)
*C08G 73/14* (2006.01)
*C08G 83/00* (2006.01)
*C08G 73/02* (2006.01)

(52) U.S. Cl.
CPC ........... *G01N 21/6428* (2013.01); *C08G 73/14* (2013.01); *G01N 21/6456* (2013.01); *G01N 33/582* (2013.01); *G01N 33/585* (2013.01); *C08G 73/028* (2013.01); *C08G 83/003* (2013.01); *G01N 2021/6441* (2013.01); *Y10S 977/707* (2013.01)

(58) Field of Classification Search
CPC .............. G01N 33/582; C08G 83/003; C08G 73/028; Y10S 977/707
USPC ......................................................... 436/172
See application file for complete search history.

(56) References Cited

U.S. PATENT DOCUMENTS 6,956,032 B1   10/2005   Waggoner
7,261,875 B2 *  8/2007   Li et al. ........................ 424/1.69

(Continued)

OTHER PUBLICATIONS

Petr A. Ledin, Frederic Friscourt, Jun Guo, and Geert-Jan Boons "Convergent Assembly and Surface Modification of Multifunctional Dendrimers by Three Consecutive Click Reactions" Chem. Eur. J. 2011, 17, 839-846.*

(Continued)

*Primary Examiner* — Christopher A Hixson
*Assistant Examiner* — Emily Berkeley
(74) *Attorney, Agent, or Firm* — Haukaas Fortius PLLC; Michael H. Haukaas

(57) ABSTRACT

The invention provides dendrimers, conjugates thereof, and methods of using dendrimer conjugates. In one embodiment, the invention provides novel polymeric dendrimers as a new class of fluorescent labels. The labels can include multiple fluorescent dye molecules conjugated to a single polymeric backbone or core, such as a dendrimer. The dendrimers can have regular or irregular branched polymeric network structures that allow for the chemical attachment of multiple dye molecules, multiple color dyes, and/or multiple functional groups, in a combinatorial fashion. The fluorescent dendritic nanoprobes (FDNs) thus provide a new class of fluorescent reporters for fluorescence microscopy and imaging.

21 Claims, 16 Drawing Sheets
(9 of 16 Drawing Sheet(s) Filed in Color)

(56) References Cited

U.S. PATENT DOCUMENTS

| | | | |
|---|---|---|---|
| 7,776,613 B2 | 8/2010 | Zhuang et al. | |
| 7,838,302 B2 | 11/2010 | Zhuang et al. | |
| 2004/0023248 A1* | 2/2004 | O'Malley | 435/6 |
| 2004/0023415 A1 | 2/2004 | Sokolov et al. | |
| 2005/0277197 A1 | 12/2005 | Chandler et al. | |
| 2008/0182336 A1* | 7/2008 | Zhuang et al. | 436/172 |
| 2010/0062460 A1 | 3/2010 | Pande et al. | |

OTHER PUBLICATIONS

Istvan J. Majoros, Thommey P. Thomas, Chandan B. Mehta, and James R. Baker Jr. "Poly(amidoamine) Dendrimer-Based Multifunctional Engineered Nanodevice for Cancer Therapy" J. Med. Chem. 2005, 48, 5892-5899.*

Bates, Mark, et al. Multicolor Super-Resolution Imaging with Photo-Switchable Fluorescent Probes, Science 317, 1749 (2007), pp. 1749-1753, DOI: 10.1126/science.1146598.

Huang, Bo, et al. Breaking the Diffraction Barrier: Super-Resolution Imaging of Cells, Cell 143, Dec. 23, 2010 Elsevier Inc., pp. 1047-1058, DOI 10.1016/j.cell.2010.12.002.

Zhuang, Xiaowei Nano-imaging with Storm, National Institute of Health Public Access Author Manuscript, 9 pgs; Published in final edited form as: Nat Photonics. 2009; 3(7): 365-367. doi:10.1038/nphoton.2009.101.

Lee, Sanghwa, et al. Single-Molecule Three-Color FRET with Both Negligible Spectral Overlap and Long Observation Time, PLoS ONE, Aug. 2010, vol. 5, Issue 8, e12270, pp. 1-9.

* cited by examiner (c)

DYE-CONJUGATED DENDRIMERS

RELATED APPLICATIONS

This application claims priority under 35 U.S.C. §119(e) to U.S. Provisional Patent Application No. 61/450,509, filed Mar. 8, 2011, which is incorporated herein by reference.

GOVERNMENT SUPPORT

This invention was made with government support under Grant Nos. R00HG004183 and R01 DK015556, both awarded by the National Institutes of Health. The United States Government has certain rights in the invention.

BACKGROUND OF THE INVENTION

Recent advances in imaging and single molecule fluorescence microscopy (SMFM) have enabled direct observation of biological processes at the molecular level.[1-3] Fluorescence-based imaging techniques rely on bright and photostable fluorescent probes with robust photophysical properties. Currently available fluorescent probes for biological labeling include fluorescent proteins,[2,4] organic dyes[1,5] and quantum dots (QDs).[6] Single organic dye molecules can be small in size (<1 nm), which facilitates non-perturbative biomolecule labeling. In addition, the photophysical properties of organic dyes can be enhanced using reducing agents and oxygen scavenger systems.[7-9] Recently, single organic dyes have enabled super-resolution imaging techniques such as stochastic optical reconstruction microscopy (STORM).[10] QDs are exceptionally bright, multi-color fluorescent probes, however, QD fluorescence emission generally exhibits transient "blinking" behavior.[11] Compared to single dye molecules, QDs are relatively large (~10-20 nm) due to their core/shell structure and further surface modification for biocompatability, which may complicate in vivo labeling and biomolecule conjugation.

Accordingly, there is a strong need to develop bright and photostable nanoscale probes for biological imaging. There is also a need for new fluorescence-based imaging compositions and techniques that provide more robust fluorescent probes than currently used fluorescent probes. Compositions and techniques that provide improved photophysical properties of fluorescent tags are also needed to advance the field of imaging and biomolecular analysis.

SUMMARY

The invention provides novel polymeric dendrimers as a new class of fluorescent labels. The labels can include multiple fluorescent dye molecules conjugated to a single polymeric backbone or core, such as a dendrimer. The dendrimers can have regular or irregular branched polymeric network structures that allow for the chemical attachment of multiple dye molecules multiple color dyes, and/or multiple functional groups, in a combinatorial fashion. The fluorescent dendritic nanoprobes (FDNs) thus provide a new class of fluorescent reporters for fluorescence microscopy and imaging.

The dendrimers described herein provide a flexible polymeric scaffold to incorporate one or more types of dye molecules and one or more types of chemical functional groups for chemical conjugation to biological molecules, cells, or tissues. The incorporation of multiple dyes results in an extremely bright and photostable fluorescent tag, compared to conventional single dye molecules. Polymeric dendrimers can be conjugated in vitro to any arbitrary biomolecule (for example, DNA, RNA, or a protein), or they can be used in vivo for targeting and labeling intracellular components. The multiple color dyes attached to dendrimer can also be used as photoswitchable sensors with various imaging techniques.

Accordingly, the invention provides dendrimer compounds of Formula I:

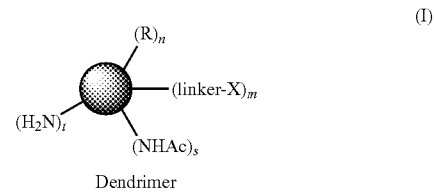

Dendrimer wherein the circle of Formula I represents the core of a G2-G10 dendrimer;

each R is independently a dye moiety covalently bonded to a branch of the dendrimer; and each linker-X is independently the same or different, wherein linker is a direct bond, a linking atom such as S, N, or O, or a chain of atoms that connects a branch of the dendrimer to a group X. The linker can be, for example, a linear or branched chain of 2-40 carbon atoms, optionally interrupted at carbon by S, N, or O at one or more locations, to provide a suitable linking group.

Each X can independently be R, a reactive group, an affinity label, or a targeting moiety; n can be a value representing about 1% to about 50% of terminal dendrimer groups; m can be a value representing 0% to about 50% of terminal dendrimer groups; s can be a value representing 0% to about 60% of terminal dendrimer groups; and t can be a value representing 0% to about 60% of terminal dendrimer groups, where the sum of n, m, s, and t=100%. Thus the sum of n, m, s, and t is equal to approximately 100% of the terminal dendrimer groups, however other substituents on the dendrimer can be included, thereby reducing the sum of n, m, s, and t to below 100%, provided that the additional substituents (groups covalently bonded to dendrimer arms) do not substantially affect the properties of the particles. The values for n, m, s, and t can be any integer within the recited range, thereby representing antecedent basis for any integer of groups within the recited percentage. For example, when the dendrimer is a G5 dendrimer, n can be about 2 to about 64; m can be 0 to about 64; s can be 0 to about 75; and t can be 0 to about 75. In another embodiment, n can be about 2 to about 32; m can be 0 to about 32; s can be 0 to about 40; and t can be 0 to about 40 for a G5 dendrimer. Such values are doubled for a G6 dendrimer, halved for a G4 dendrimer, and similar modifications are made for other generation dendrimers.

In some embodiments, at least two R groups are different from each other. In other embodiment, each R group is the same.

The invention also provides dendrimer compounds of Formula II:

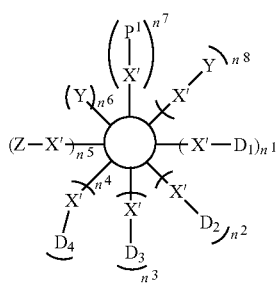

(II)

wherein $n^1$, $n^2$, $n^3$, $n^4$, $n^5$, $n^6$, and $n^8$ are each independently 0-20, and/or each represents a value corresponding to 0% to about 60% of the terminal groups on the dendrimer surface. While other terminal groups can be present, the sum of $n^1$, $n^2$, $n^3$, $n^4$, $n^5$, $n^6$, and $n^8$ will substantially equal the total number of terminal groups of the dendrimer. The circle at the core of Formula II represents a dendrimer moiety having a diameter of about 2 nm to about 15 nm, 2 nm to about 10 nm, or about 3 nm to about 7 nm, wherein the dendrimer core comprises a chemically symmetrical or unsymmetrical polymer backbone or hyperbranched polymer backbone.

Each X' is independently linker as described above for Formula I, or a linking group selected from —O—, —NH—, —CO$_2$—, —OCO$_2$—, —S—, —P(O)(OR)O—, —NH(CO)O—, —NH(CO)—, —NH(CS)NH—, —SO$_2$—, —SO$_3$—, —(CH$_2$)$_n$— where n is 1-10, and the like, or X' is a direct bond to a nitrogen atom or oxygen atom of the dendrimer core;

each Y and Z is independently —OH, —NH$_2$, —CO$_2$H, —COOR', —SR', —P(O)(OR')$_2$, —OC(O)OR', —NH(CO)OR', —NH(CS)NHR', —SO$_2$R', —SO$_3$R', or the like, where each R' is independently an alkali metal, alkaline earth metal, hydrogen, vinyl, (C$_6$-C$_{10}$)aryl, (C$_1$-C$_{12}$)alkyl, or a chemical functional group for bioconjugation, such as biotin, alkyne, azide, tetrazine, alkene, vinyl sulfone, an active ester such as an N-hydroxysuccinic ester, pentafluorophenyl ester, tetrafluorophenyl ester, pentafluoroethyl ester, or the like, an active carbonate such as 4-nitrophenoxy carbonate, pentafluorophenoxy carbonate, or the like, an active carbamate such as 4-nitrophenoxy carbamate or a pentafluorophenoxy carbamate, benzylguanine, or O2-benzylcytosine;

$D_1$, $D_2$, $D_3$, and $D_4$ are each independently a dye moiety, which can be the same or different, bonded to a group X'; and $P^1$ is a (C$_1$-C$_{12}$)acyl group, such as an acetyl group, or a poly- or oligo-ethylene glycol moiety (e.g., having 2 to about 500 repeating units) linked by an amide or carbonate to X'; or salt thereof. Dendrimers of Formula II can be dendrimers of Formula I, or they can be separate embodiments.

The diameter of the dendrimer can be, for example, less than about 30 nm, less than about 20 nm, less than about 15 nm, or less than about 8 nm, and in some embodiments, the dendrimer can include a cation or anion and optionally a counterion, thereby forming a salt.

The dendrimer can be a poly(amidoamine) (PAMAM) dendrimer or any other water soluble dendrimer. Such dendrimers can therefore be useful for biological labeling. In specific embodiments, the dendrimer can be, for example, a G3, G4, G5, G6, G7, or G8 dendrimer.

The group linker-X can include one or more ethylene glycol units, one or more (C$_1$-C$_6$)amide units, one or more (C$_1$-C$_{20}$)alkyl chains, or a combination thereof. The group X can include an alkyne, an azide, an N-hydroxysuccinimide (NHS)-ester, a pentafluorophenyl ester, a tetrafluorophenyl ester, a pentafluoroethyl ester, a vinylsulfonyl group, a 2-pyridyldisulfide, a methansufinyldisulfide, a 4-nitrophenylcarbonate group, a 4-nitrophenylcarbamate group, a thiol, or an imide group. For example, the group X can include dibenzocyclooctyne (DBCO) conjugated to the dendrimer through a polyethylene glycol chain (e.g., DBCO-PEG2-10, such as DBCO-PEG4). In some embodiments, the group X can also be biotin or a Ni/Co-NTA group.

In various embodiments, the group R can be a fluorescent dye. For example, R can be Acridine Orange, Acridine Yellow, an Alexa Fluor dye, a CF™ dye (e.g., a dye antibody conjugate) (available from biotium.com), an Atto dye, a BODIPY dye, Cascade Blue, coelenterazine, coumarin, a cyanine dye, a dansyl dye, 4',6-diamidino-2-phenylindole (DAPI), erythrosin, FLUO 3, fluorescein, FURA 2, 5-hydroxytryptamine (HAT), a Hoechst dye, INDO 1, JC-1 dye, Lucifer Yellow, Nile Red, Oregon Green dye, propidium iodide, QUIN 2, a rhodamine dye, R-phycoerythrin, R-phycoerythrin-Texas Red, SNARF, or Texas Red. Specific examples of R include one or more of Cy2, Cy3, Cy3.5, Cy5, Cy5.5, or Cy7.

The molecular diameter of the dendrimer can be less than about 30 nm, less than about 20 nm, less than about 15 nm, less than about 12 nm, less than about 10 nm, less than about 8 nm, less than about 6 nm, less than about 5 nm, or less than about 4 nm. For example, the can be about 2 nm to about 10 nm, about 2 nm to about 7 nm, or about 2 nm to about 5 nm.

The dendrimer can have one or more free amine groups at the surface of the dendrimer, and/or one or more free carboxyl groups at the surface of the dendrimer. The dendrimer chains can also terminate in N-acetyl groups or optionally protected carboxyl groups.

The dendrimer can exhibit multiple emission wavelength colors upon excitation to provide a plurality of distinct fluorescent signatures. The photobleaching lifetime of the dendrimer can be, for example, more than 2 times longer, or more than 5 times longer than the photobleaching lifetime of a single dye, for example, under similar conditions separate from a dendrimer. The fluorescence emission intensity can be at least two times brighter than a corresponding single dye, such as 3×, 4×, 5×, or 6× brighter.

In some embodiments, about 2% to about 25%, or about 4% to about 15% of the terminal groups of the dendrimer comprise surface bound dye moieties, for example, about 6-12 for a G5 dendrimer. In some embodiments, about 4% to about 15% of the terminal groups of the dendrimer comprise surface bound linker-X groups or other substituent groups as described for Formulas I and II, for example, about 6-12 for a G5 dendrimer. In some embodiments, one or more of the linker-X groups comprise biotin or a Ni/Co-NTA group. In some embodiments, each of the dye moieties is located within a distance of about 12 nm, about 10 nm, about 8 nm, or about 6 nm, on the dendrimer surface, for example, within about 5-15 nm, within about 7-12 nm, or within about 8-10 nm.

The invention also provides a fluorescent probe comprising two or more different dyes conjugated to a dendrimer, wherein at least two of the dyes emit light at different wavelengths upon irradiation, and the molecular diameter of the fluorescent probe is less than about 20 nm.

The invention also provides a method to provide a distinct spectral fingerprint to a single molecule comprising conjugating to a molecule a fluorescent probe as described herein, wherein the fluorescent probe comprises two or more different color dyes conjugated to the dendrimer of the probe, thereby providing a single molecule with a multiple wavelength emission when irradiated by two or more excitation light sources that correspond to the absorption spectra of the dyes of the probe.

The invention further provides a method for labeling a biomolecule that includes contacting a sample with a plurality of dendrimers as described herein, wherein a reactive group of the dendrimer conjugates the dendrimer to the biomolecule, thereby allowing detection by microscopy. The biomolecule can be, for example, DNA, RNA, a protein, a membrane, or an intracellular component, such as a peptide or carbohydrate.

The invention also provides a method for in vivo targeting and labeling an intracellular components comprising contacting one or more intracellular components with a plurality of dendrimers described herein, wherein a reactive group of the dendrimer conjugates the dendrimer to one or more of the intracellular components, thereby allowing detection by microscopy. The microscopy can include, for example, fluorescence microscopy.

The invention further provides a method of imaging a sample that includes photoswitchable fluorescent probes. The method can include:

(a) providing a sample labeled with a plurality of photoswitchable fluorescent probes, wherein the photoswitchable fluorescent probes comprise one or more dendrimers as described herein, at least some of the dye moieties of the photoswitchable fluorescent probes being in a state not capable of emitting light at a first wavelength;

(b) exposing the plurality of photoswitchable fluorescent probes to substantially identical activation light to activate a statistical subset of the photoswitchable fluorescent probes from a state not capable of emitting light at the first wavelength to a state capable of emitting light at the first wavelength;

(c) exciting the activated subset of photoswitchable fluorescent probes with excitation light to cause the activated subset to emit light at the first wavelength;

(d) determining light emitted at the first wavelength by the activated subset of photoswitchable fluorescent probes;

(e) substantially deactivating the activated subset of photoswitchable fluorescent probes;

(f) repeating (b) through (e) one or more times, each time activating a statistically different subset of the plurality of photoswitchable fluorescent probes; and (g) determining the positions of at least some of the photoswitchable fluorescent probes within the sample by using the light emitted by the activated subsets of the photoswitchable fluorescent probes. Related techniques are described in U.S. Pat. No. 7,776,613 (Zhuang et al.) and U.S. Pat. No. 7,838,302 (Zhuang et al.).

The invention therefore provides novel dendrimers of Formula I or II, intermediates for the synthesis of dendrimers of Formula I or II, as well as methods of preparing dendrimers of Formula I or II. The invention also provides dendrimers of Formula I or II that are useful as intermediates for the synthesis of other useful dendrimers. The invention further provides methods of using the dendrimers described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

Figure 1:
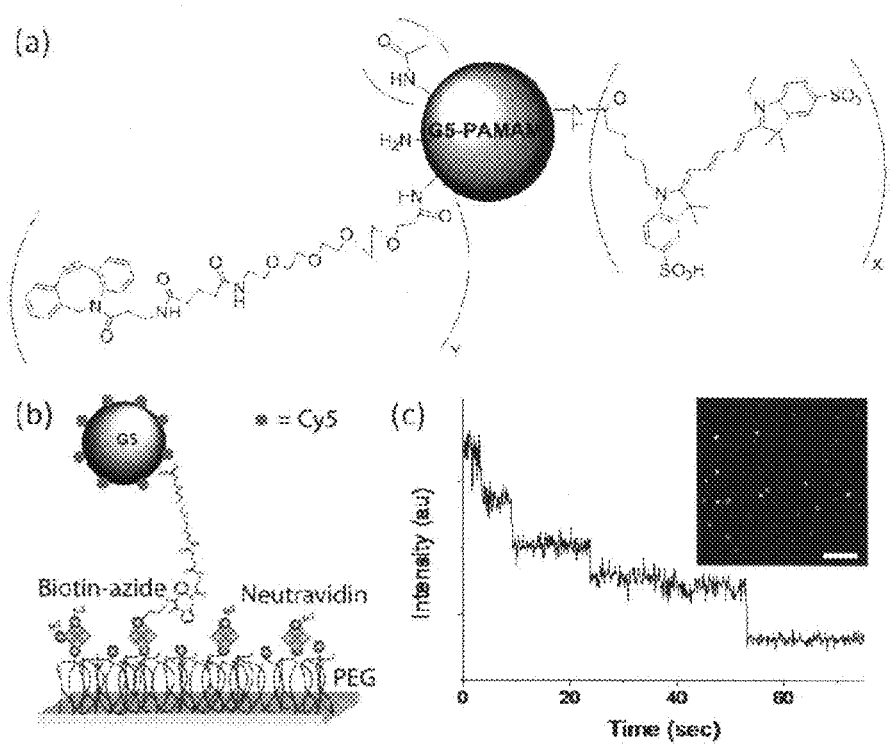
FIG. 1. (a) Chemical structure of dye-conjugated PAMAM dendrimer, with x=8 (Cy5) and y=9 (DBCO), an example of a fluorescent dendritic nanoprobe (FDN). (b) Schematic of surface attachment scheme for single molecule imaging. Dendrimer-Cy5-DBCO is linked to a coverslip surface using Cu-free click chemistry via an azide-biotin linker and covalently-grafted PEG/PEG-biotin. (c) Fluorescence intensity trajectory for a single dendrimer-Cy5 molecule (10.9 kW/cm$^2$ laser intensity). Inset: image of single dendrimer molecules. Scale bar: 4 µm. (d) A Generation 2 polyamidoamine (G2 PAMAM) dendrimer, which can serve as a core of the substituted dendrimers described herein. The G2 dendrimer can be modified to include additional generations of branches to provide other dendrimers, such as G3-G10 dendrimers having dye, functional group, or blocking group substituents.
Figure 1D:
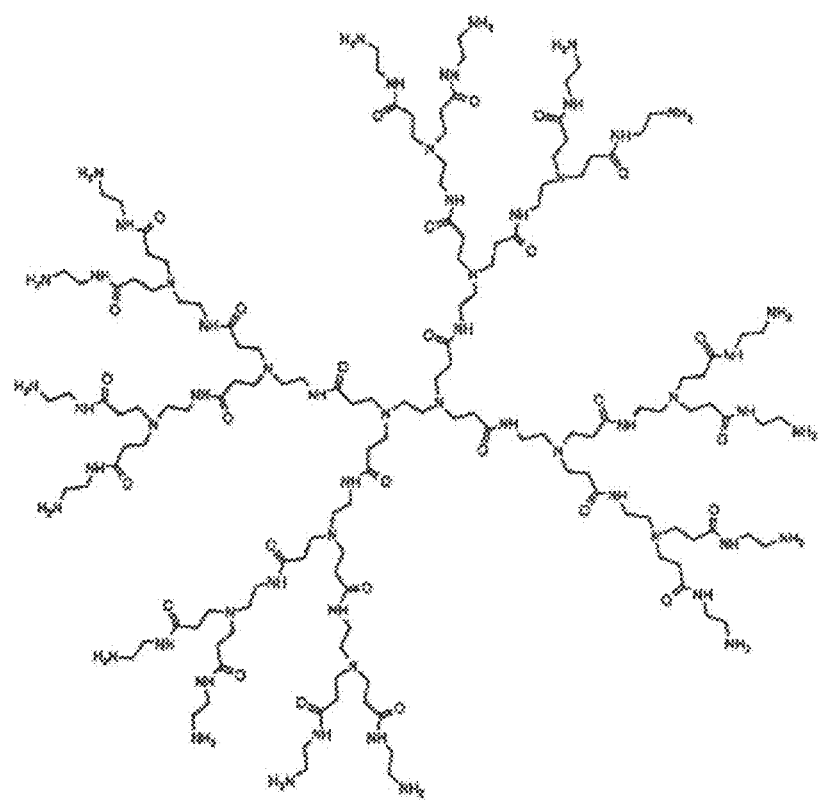

The invention provides dye-conjugated dendrimers as bright and photostable nanoprobes for fluorescence microscopy and imaging, and other uses. The dendrimers described herein provide useful tools for analysis of a variety of compositions, and can be used in conjunction with single molecule fluorescence microscopy (SMFM). The dendrimers can also be used for multi-color combinatorial dye conjugation, and as novel labels for super-resolution microscopy.

The dendrimer compounds described herein thus provide novel labeling technology. Various dendrimers, such as different generations of polyamidoamine (PAMAM) dendrimers, can be modified to include specific chemical functionalities at their surface or within the core of the dendrimer, including substituents such as biotin, alkynes, and/or other functional groups combined with specific fluorophores, and the like. Using dendrimers as fluorescent tags provides significant advantages for labeling, enabling combinatorial dye conjugation and related techniques.

The dendrimers can contain various fluorescent dye molecules such as commonly used commercial dyes and/or derivatives thereof. A wide variety of dyes can be readily conjugated to free amine groups or carboxy groups at the surface of the dendrimers. The free amine groups can also be conjugated to linkers to provide other functional groups at the surface of the dendrimers, such as hydroxyl groups or carboxylic acids, to facilitate conjugation of other dyes. Techniques for conjugating dyes to functional groups (such as amines, hydroxyls, or carboxylic acid groups on the surface of a dendrimer) are standard transformations and are well known in the art. Such techniques are described by, for example, by Greg T. Hermanson in *Bioconjugate Techniques*, Academic Press, San Diego, Calif. (1996). Examples of dyes that can be conjugated to dendrimers include the cyanine dyes and variations thereof, such as those described in U.S. Pat. No. 6,956,032 (Waggoner); U.S. Pat. No.

7,671,214 (Leung et al.); U.S. Pat. No. 7,776,613 (Zhuang et al.); and U.S. Pat. No. 7,838,302 (Zhuang et al.); U.S. Patent Publication Nos. 2010/0062460 (Pande et al.); and 2004/0023415 (Sokolov et al.); and various known dyes such as Alexa Fluor 405, Alexa 647, cyanine dyes such as Cy2, Cy3 and various red cyanine dyes such as Cy5, Cy5.5 and Cy7, Dylight dyes such as DyLight 488, 549, 633, 649, 680 and 800, ATTO dyes, and xanthene type dyes.

The dendrimer technology described herein provides numerous advantages over single dye techniques. Using combinatorial dye combinations with two or three different color dyes linked to a dendrimer, a large number of distinct spectral wavelength signatures are created. These signatures cannot be achieved using existing technologies because dendrimers are small, nanoscale molecular scaffolds that enable specific linking of multiple dyes to a single macromolecule, thereby generating a fluorescent label with multiple emission wavelengths (colors) within a single molecule. Alternative strategies to achieve the same effect (multiple colors) include large, micron to millimeter sized beads, wherein multiple colors dyes are linked, however these labels are very large, much larger than nanoscale dendrimers. In addition, multiple color quantum dots can be 'packed' into large, millimeter sized beads, but these beads are too bulky, large and massive to be used as labels for biomolecules, and they are generally used immobile (stationary) labels. Finally, dendrimers can be synthesized to be nearly monodisperse, which is a clear advantage over using linear polymer chains as nanoscale macromolecular fluorescent probes.

Additionally, combinatorial dye detection requires only 2-3 different colors and only 2-3 different excitation (illumination) light sources. Therefore, only ~2 different excitation sources are required to generate at least 6-10 or more different colors (distinct spectral signatures) (see FIG. 11). Conventionally, when 6 different color dyes are used for a molecular imaging or biological probing system, up to 6 different light sources are required. However, it is generally not practical or even possible to utilize 6 different lasers or light sources in relevant lab analyses.

Furthermore, fluorescent dyes conjugated to polymeric dendrimers exhibit 3-20× longer fluorescence photobleaching lifetimes compared to single dye molecules, as well as 2-10× brighter fluorescence emission intensity compared to single dyes, for Cy5 conjugated 6th generation PAMAM dendrimers. Because larger generation of polymeric dendrimers can contain more dye molecules, additional dyes can improve the brightness and stable photon emission. This was demonstrated by comparing eight Cy5 dye conjugated 5th generation PAMAM dendrimer and fifteen Cy5 dye conjugated 6th generation PAMAM dendrimer. The improvement in fluorescence photobleaching lifetimes is an important advantage and was not expected a priori. Overall, conventional fluorescent dyes suffer from short lifetimes or low fluorescence emission that limits detection resolution. The dye-conjugated polymeric dendrimers described herein solve these issues by providing labels with longer lifetimes and stronger fluorescence emissions to enable greater detection resolution.

Figure 7:
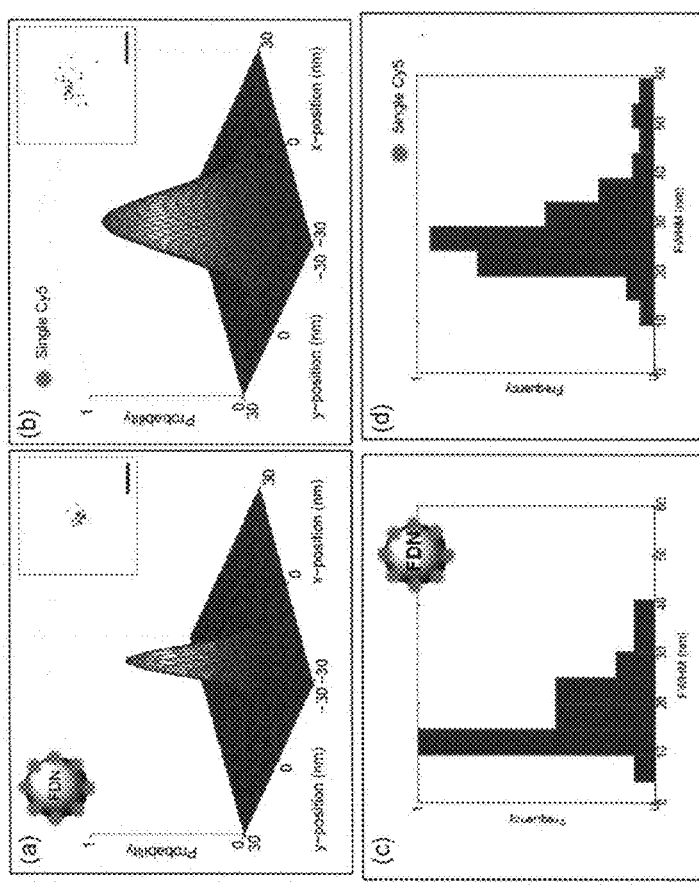
FIG. 7. (a) Localization precision for (a) Cy5-FDNs and (b) single Cy5 dyes determined using single molecule fluorescence microscopy. The centroid position for a single fluorescent probe is determined by Gaussian mask estimation over successive images (inset), and the distribution of centroid positions was fit to a 2D Gaussian function. The localization precision for Cy5-FDNs (G5 PAMAM with 8 Cy5 dyes) and single Cy5 dyes was found to be 6.0 nm and 9.8 nm (determined as standard deviation of the 2D Gaussian), or 14 nm and 23 nm (determined as FWHM), respectively. Inset scale bar: 20 nm. Localization precision for (c) Cy5-FDNs and (d) single Cy5 dye molecules determined as FWHM (full width half maximum) of a 2D Gaussian function. In all cases, the 2D Gaussian function was fit to the distribution of centroid positions determined from >30 consecutive images of the same probe. Images were acquired using 35 mW laser power excitation (measured at the source) and a 400 msec integration time. The modes of the distributions for Cy5-FDN and single Cy5 dyes are 12.5 nm and 27.5 nm, respectively.

Fluorescent nanoprobes containing multiple dye molecules can enhance localization precision. The point spread function (PSF) was calculated using two-dimensional (2D) Gaussian fitting to localize fluorescent dendrimers with sub-diffraction accuracy, and the precision of centroid determination for single Cy5-dendrimers and single Cy5 molecules was determined (FIG. 3b). Overall, the localization precision for Cy5-dendrimers is enhanced compared to single Cy5 dyes due to increased brightness. Because Cy5-dendrimers and single Cy5 molecules yield diffraction limited images, the FWHM for the 2D Gaussian fit should be similar. However, brighter fluorescent tags can yield smaller FWHM, and a modest decrease in the FWHM was observed for Cy5-dendrimers containing multiple dyes (FIG. 7).

Photoswitchable dendrimers have also been prepared. Photoswitchable dendrimers are novel materials and provide the first demonstration of photoswitching on a single macromolecule with multiple dyes. Applicants have demonstrated that multiple (Cy5) dyes on a dendrimer can initially be in a dark, non-emissive state. The dendrimer can then be exposed to a short pulse of light to activate some or all of the dyes contained in the dendrimer, thereby switching it to an active state. The position of the dendrimer can then be determined by localization. Thereafter, the dendrimer return to a dark, non-emissive state. Applicants have also showed that this process can be repeated, which enables stochastic cycling of dendrimer activation/deactivation, thereby enabling super-resolution imaging with extremely bright nanoprobes.

Finally, dendrimers are a simple and user-friendly concept for labeling. Dendrimers can contain multiple and versatile chemical functionalities for biomolecule labeling. New polymeric dyes can improve the resolution of fine microscopy techniques, using most popular and existing microscopy set ups such as green and red laser setups.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation off ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "dendrimer" refers to a regular or irregular branched polymeric network structure such as a branched molecule built from interconnected natural or synthetic monomeric subunits. Dendrimers are well known in the art. Examples of dendrimer and methods for preparing them are described by, for example, U.S. Pat. No. 5,338,532 (Tomalia et al.), U.S. Pat. No. 5,739,218 (Dvornic et al.), U.S. Pat. No. 6,077,500 (Dvornic et al.), U.S. Pat. No. 6,730,334 (Zhao), and U.S. Pat. No. 7,872,072 (Bentley et al.). Data for various PAMAM dendrimer generation cores are shown in the table below.

| Generation | Molecular Weight | Measured Diameter (Å) | Surface Groups |
|---|---|---|---|
| 0 | 517 | 15 | 4 |
| 1 | 1,430 | 22 | 8 |
| 2 | 3,256 | 29 | 16 |
| 3 | 6,909 | 36 | 32 |
| 4 | 14,215 | 45 | 64 |
| 5 | 28,826 | 54 | 128 |
| 6 | 58,048 | 67 | 256 |
| 7 | 116,493 | 81 | 512 |
| 8 | 233,383 | 97 | 1024 |
| 9 | 467,162 | 114 | 2048 |
| 10 | 934,720 | 135 | 4096 |

The term "fluorescence photobleaching lifetime" refers to the total time before the fluorescence signal decays to zero for a single dendrimer.

The term "functional group" with respect to a dendrimer substituent refers to a group covalently bonded to a dendrimer, optionally through a linker, where the functional group has a use in biological analysis. The functional group can be an affinity label, an alkyne or azide for copper-free click chemistry, biotin, or other groups that facilitate target specific conjugation to a biomolecule. The terminal amine groups of a dendrimer are not considered substituents for the purposes of this definition of the term functional group.

Chemical functional groups for bioconjugation include, but are not limited to, groups such as biotin, alkyne, azide, tetrazine, alkene, vinyl sulfone, an active ester such as an N-hydroxysuccinic ester, pentafluorophenyl ester, tetrafluorophenyl ester, pentafluoroethyl ester, or the like, an active carbonate such as 4-nitrophenoxy carbonate, pentafluorophenoxy carbonate, or the like, or an active carbamate such as 4-nitrophenoxy carbamate, a pentafluorophenoxy carbamate, and the like.

A reactive group is a chemical functional group that reacts with a group found on a biomolecule (e.g., on its surface) to form a conjugate through a covalent bond.

An affinity label is a chemical functional group that associates with one or more groups of a biomolecule to form a conjugate through electrostatic interactions.

A targeting moiety can be, for example, a cell targeting moiety such as an antibody, an antibody fragment, a growth factor, a hormone, a peptide, an aptamer, or a cytokine. The antibody can be a full-length antibody, chimeric antibody, Fab', Fab, F(ab')2, single domain antibody (DAB), Fv, single chain Fv (scFv), minibody, diabody, triabody, an Affibody® molecule, or a mixture thereof. Further examples of useful targeting moieties are described in U.S. Patent Publication No. 2006/0263368 (Rosenblum et al.). Information on Affibody® molecules can be found at affibody.com/en/.

Fluorescent dyes include, but are not limited to, Acridine Orange, Acridine Yellow, an Alexa Fluor dye, an Atto dye, a BODIPY dye, Cascade Blue, coelenterazine, coumarin, a dansyl dye, 4',6-diamidino-2-phenylindole (DAPI), erythrosin, FLUO 3, fluorescein, FURA 2, 5-hydroxytryptamine (HAT), a Hoechst dye, INDO 1, JC-1 dye, Lucifer Yellow, Nile Red, Oregon Green dye, propidium iodide, QUIN 2, a rhodamine dye, R-phycoerythrin, R-phycoerythrin-Texas Red, SNARF, Texas Red, and cyanine dyes, such as Cy2, Cy3, Cy3.5, Cy5, Cy5.5, or Cy7. Many dyes described herein are photoswitchable dyes. Additional examples include Dronpa, bsDronpa, Eos, enhanced yellow fluorescent protein (EYFP), red cyanine dyes, Cy5/Alexa 647, and rhodamine and oxazine dyes. Other useful dyes and techniques are described in U.S. Patent Publication No. 2005/0277197 (Chandler et al.).

Dye-Conjugated Dendrimers

Polymeric dendrimers containing multiple dyes and combinatorial dye color combinations have been prepared and evaluated. Various dendrimers have been prepared to include versatile chemical functionalities such as alkynes and azides for click chemistry, biotin for affinity labeling, etc. In various embodiments, the dendrimers can be conjugated to targeting ligands, for example, for in vivo imaging with minimal toxicity. The photophysical properties of single dye-conjugated dendrimer molecules immobilized to chemically modified surfaces were characterized using total internal reflection fluorescence microscopy (TIRF-M). Fluorescence photobleaching lifetimes of dye-conjugated dendrimers were observed to far exceed the lifetimes of single conventional organic dye molecules, both in the presence or absence of oxygen scavengers.

Single dendrimer molecules were also found to be significantly brighter than single conventional organic dye molecules. Furthermore, the precision of centroid position determination for single molecule localization was determined by fitting the fluorescence emission from single dendrimers to a 2-dimensional Gaussian function. Thus, dye-conjugated dendrimers exhibit several advantages over single dyes and quantum dots for use as fluorescent tags for labeling biological molecules.

The dendrimers described herein provide facile access to photo-switchable molecules and formulations from one macromolecular scaffold. Multi-dye combinations on one scaffold can provide an optimized ratio between activator and fluorescence emitter molecules for super-resolution fluorescence microscopy. Brighter multi-dye conjugated dendrimers will enable researchers to achieve higher resolution images than when conventional single organic dyes or fluorescent proteins are used. Multi-dye conjugated dendrimers molecules can be used for in vivo super resolution imaging via primary antibody conjugation or secondary antibody conjugation because the dendrimers are bio-compatible.

Dye-conjugated dendrimers have been developed as nanoscale imaging probes for fluorescence microscopy. Generation-5 polyamidoamine (PAMAM) dendrimers were synthesized to contain multiple dye molecules, and the photophysical properties were characterized using single molecule fluorescence microscopy. Single dendrimer molecules showed highly extended photobleaching lifetimes (8-10×) and enhanced localization precision compared to single dyes. The dye-conjugated dendrimers are small (~5-6 nm), bright, photostable and contain a variety of surface chemical functionalities for facile conjugation to target biomolecules.

An alternative class of fluorescent probes based on chemically-modified, dye-labeled dendritic polymers is described herein. Dye-conjugated dendrimers containing multiple covalently-linked organic dye molecules within a single nanometer-sized macromolecule (4-5 nm) were synthesized, thereby generating bright and photostable fluorescent probes suitable for high resolution imaging methods. Dendrimers are polymers having highly regular branched structures with large numbers of terminal functional groups.[12,13] Compared to linear macromolecules, dendrimers can be synthesized with controlled, nearly monodisperse sizes, which is a key advantage for labeling probes. Dendrimers have been extensively used for gene and drug delivery and diagnostic applications via live cell or animal imaging.[13] Previous work on fluorescent dendrimers[14] has focused on light-harvesting macromolecules[15] and water-soluble optically-active dendrimers which complex DNA.[16] Recently, DNA templated assembly of dendrimers was demonstrated using covalent coupling via click chemistry.[17]

Polyamidoamine (PAMAM) dendrimers were used as molecular scaffolds to assemble multiple dyes and functional groups, including cyanine dyes (Cy3/Cy5), biotin, dibenzocyclooctyne (DBCO) for copper-free click chemistry and acetyl groups for controlling surface charge. PAMAM-amine dendrimers serve as model dendritic polymers for fluorescent probes due to an intrinsic capacity for surface functionalization. Using SMFM, it was shown that single dendrimer molecules conjugated with multiple cyanine dyes exhibit enhanced photophysical properties compared to single dye molecules, including exceptional photostability and substantially increased fluorescence photobleaching lifetimes, defined as fluorescence "on-time" before bleaching to a dark state. Overall, dye-conjugated dendrimers represent "all-in-one" inclusive nanoimaging probes that can be synthesized to contain multiple organic dyes and a variety of orthogonal linker moieties, which allow for facile conjugation to target molecules.

The dendrimers described herein typically employ the generation-5 PAMAM scaffold, however other generation PAMAM-amine dendrimers can also be employed. Examples of other PAMAM-amines include generations 2, 3, 4, 6, 7, 8, 9, and 10, each generation having double the number of surface functional groups of the previous generation, and each generation can be used to provide varied properties and surface functionalization of the resulting probes. A variety of dendrimers are commercially available from providers such as Dendritech (Midland, Mich.; dendritech.com/pamam.html).

Applications of Dye-Conjugated Dendrimers

Single Molecule Fluorescence Microscopy.

Multi-dye conjugated dendrimers can be used as novel fluorescent tags for single molecule detection. Fluorescent labels used for single molecule microscopy need not be single dye molecules. Dye-conjugated polymeric dendrimers offer several advantages over conventional "single dye" molecules, including enhanced brightness and fluorescent intensity emission and extremely long fluorescence photobleaching lifetimes compared to single dyes. For example, dye-conjugated dendrimers can exhibit at least a 10× increase in their fluorescence photobleaching lifetimes compared to single dyes. The advantages of over single dyes also include the capability for combinatorial color imaging. Finally, the dendrimer size is comparable to fluorescent proteins and therefore it is small enough to be used in protein structural study and related applications, which is an advantage over quantum dots, which are large in size (10-20 nm), which makes them perturbative toward biological labeling in many cases because they perturb biological function.

Multi-Color Combinatorial Dye Conjugation.

Incorporating multiple color dyes within a single dendrimer provides a combinatorial fluorescent tag analogous to a multi-color "bar-code" with a distinct spectral fingerprint.

By conjugating variable ratios of two or three different color dyes into dendrimers, each single dendrimer exhibits multiple colors (multiple wavelength emission), which increases the number of distinct fluorescent "signatures" in a combinatorial fashion. For example, two colors can be incorporated in a single dendrimer in variable ratios, thereby resulting in multiple distinct tags from only 2 colors. Methods of analyzing multiple fluorescent signals are known in the art and are described by, for example, U.S. Publication No. 2005/0277197 (Chandler et al.).

Multi-color dye-conjugated dendrimers also exhibit extremely long fluorescence photobleaching lifetimes (for example, $t_{1/2}$=greater than 300 seconds at 1.1 kW/cm$^2$ laser intensity), which enables researchers to probe complex biomolecular systems that could not be probed with traditional single dye labeling strategies. Currently, fluorescence labeling using single organic dyes suffers severe limitations because each single dye requires a distinct excitation light source. However, if two dyes are used to generate multicolor labeling by combinatorial dye conjugation on a dendrimer, only two excitation light sources are required to create multiple color labels. A dendrimer with three dyes conjugated to the surface can provide even more diverse detection schemes.

Novel Labels for Super-resolution Microscopy.

Dendrimers containing multiple fluorescent dye molecules serve as extremely bright fluorescent labels for high-resolution or "super-resolution" microscopy, including STORM imaging. The dendrimers have been demonstrated to be photoswitchable, which enables super-resolution imaging. Because dye-conjugated dendrimers are brighter than single dye molecules, dendrimers will provide enhanced precision of centroid determination, and therefore enhanced resolution, compared to existing methods for super-resolution microscopy relying on traditional, single organic dye molecules such as traditional STORM. Super-resolution microscopy is a valuable technique for biological imaging.

In various embodiments, the invention provides the following compositions and methods.

Combinatorial Dye Labeling.

Dye-conjugated dendrimers enable multi-color detection and labeling, a novel technology using single molecules as probes. By incorporating multiple color dyes using a combinatorial conjugation scheme onto a dendrimer, two or three different color dyes naturally generate an extremely large number of spectral wavelength patterns in an "optical bar-coding" fashion. Overall, this method overcomes many limitations of using single dyes. For example, to create 6, 10, or more distinct optical wavelength signatures, only two or three different dyes are required. In some embodiments, only 1 or 2 different light sources are required to provide suitably distinct optical wavelength signatures. Traditionally, to obtain 6 or 10 colors, the same (e.g., 6 or 10) number of light sources is required, which is intractable and not practically or economically feasible.

Flexible Chemical Functionalization.

Multi-dye conjugated dendrimers can be modified and functionalized, thus enabling facile conjugation to arbitrary biomolecules, such as DNA, RNA, proteins, and/or membranes. Multiple chemical groups can be included on a dendrimer, including alkynes and cycloalkynes such as cyclooctynes, and/or azides for click chemistry, biotin and/or Ni/Co-NTA for affinity labeling, active ester such as NHS-esters, pentafluorophenyl esters, tetrafluorophenyl esters, pentafluoroethyl esters, 4-nitrophenyl carbonates, or 4-nitrophenyl carbamates for amine conjugation, and imides, vinylsulfones, 2-pyridyldisulfides, and/or methansulfinylsulfides for thiol conjugation (see Hermanson, *Bioconjugate Techniques*, Academic Press, San Diego, Calif. (1996)). In addition, chemical functionalities can be incorporated into to a probe, thereby allowing for tetrazine cycloaddition reactions, which provide an additional class of facile chemical coupling reactions for biological molecules.

Fluorescent Tags for Super-Resolution Microscopy, STORM, or (F)PALM Imaging.

Currently, there are no fluorescent labels on the market containing multiple dye molecules that would enable single molecule detection with <1 nanometer precision. Dendrimers are nanometer-sized molecules (2-4 nm in diameter, in some embodiments), which is suitably small and appropriate for single molecule detection and super-resolution microscopy. Dendrimers can be used for nanometer resolution imaging, as described herein, thereby providing technology for single molecule imaging. The Cy3 and Cy5 labeled dendrimers can be used as photoswitchable probes for improving STORM imaging. High intensity and narrow centroid determination can also improve (F)PALM imaging. The increased intensity and small size of the dendrimer conjugates described herein can help improving detection and localization by narrowing centroid determination and improving accuracy of point spread functions.

Novel Materials for In Vivo Labeling.

The polymeric dendrimers described herein provide a new class of fluorescent tags for in vivo labeling, with several advantages over inorganic materials such as quantum dots. Due to their small size (approximately 2-4 nm), dendrimers can be effectively cleared from the liver and kidneys, thereby removing the limitation of toxicity encountered with large quantum dots (~20+ nm).

Because the dendrimer size can be very small (2-4 nm; more than 5 or 10 times more compact than quantum dots (20+ nm)), the dendrimers can safely be used for in vivo imaging applications. Quantum dots suffer from the key disadvantages of relatively large size and inorganic material composition, which can lead to cytotoxicity. The large size of QDs prevents their clearing from the liver and kidneys. Due to their smaller size, dendrimers will not suffer from these limitations. Although the fluorescence lifetime of polymeric dendrimers may be shorter than quantum dot lifetimes, dendrimers provide a significantly improved fluorescence photobleaching lifetimes (5-20 times longer than single dyes) as well as an enhanced emission intensity (about 5 to about 10 times brighter compared to single dyes), which are excellent properties for single molecule fluorescence microscopy.

The surface modification of QDs is less robust than for dendrimer because chemically grown dendrimers can inherently terminate in biocompatible functional groups such as —SR, —CO$_2$R, —OH, —NH$_2$, —P(O)(OR)$_2$, —SO$_3$R, and the like, where R can be a variety of groups such as hydrogen, alkali metals, or alkali earth metals, whereas QDs require surface modification for biocompatibility. An additional layer of polymer coating on a QD surface or other types of surface modification of QD surfaces cannot provide the robust bioconjugation obtainable using the dendrimer described herein.

Fast and Reliable Labeling of General Biological Materials.

The technology described herein provides a new concept of dye labeling and a novel route to general biomolecule labeling. The technology further enables enhanced precision for single molecule imaging compared to current techniques.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Dye-Conjugated Dendrimers

Multiple amine-reactive Cy5-NHS or Cy3-NHS (N-hydroxysuccinimide) ester dyes were linked to generation-5 (G5) or generation-6 (G6) PAMAM-amine dendrimers. G5 and G6 PAMAM dendrimers are ~5 nm and ~6 nm in diameter and contain approximately 128 and 256 surface amine groups, respectively.

In one example, generation-5 PAMAM-amine (G5-$NH_2$) dendrimers were used as a macromolecular scaffold for organic dyes. G5 PAMAM dendrimers exhibit an overall molecular diameter of ~5 nm and contain 128 surface amine groups. Multiple amine-reactive Cy5-NHS ester dyes were linked to dendrimer molecules, thereby yielding G5 dendrimers bearing an average of 8 surface-bound Cy5 molecules, as determined by mass spectrometry.

Samples of PAMAM dendrimers were further functionalized with biotin or dibenzocyclooctyne (DBCO) for click chemistry to enable target-specific labeling of biomolecules or surface immobilization for single molecule fluorescence microscopy. After each successive addition reaction, the average degree of dye or chemical substitution was quantified by MALDI-TOF (matrix-assisted laser desorption/ionization) mass spectrometry analysis. In this way, the extent of fluorescent dye loading could be control between about 1 and about 15 dye molecules for PAMAM dendrimers. To prevent additional reactions or premature degradation, a fraction of the amine groups on PAMAM dendrimer surfaces was blocked with acetyl groups. At neutral pH, the remaining amine groups are protonated to yield surface ammonium ions (R—$NH_3^+$). Electrostatic interactions mediated by positive surface charges were sufficient to prevent interactions between dendrimers, and between dendrimers and target proteins, thereby minimizing non-specific interactions upon conjugating dendrimers to proteins for imaging or SMFM. Following chemical synthesis and purification, FDNs remained stable for several months upon storage at 4° C.

Materials and Synthesis.

The following materials and reagents were used: PAMAM dendrimer Generation 5 and 6 (Sigma Aldrich, MO), dibenzocyclooctyne acid N-hydroxysuccinimidyl (NHS) ester (DBCO) (Click Chemistry Tools, Macon, Ga.), PEG5000-NHS ester (Laysan Bio, AL), NeutrAvidin (Pierce Biotechnology), Amicon 10K MW cutoff membrane filter (Millipore), and glass slides and coverslips (Fisher Scientific). Cyanine dyes (Cy3-NHS ester and Cy5-NHS ester) were synthesized as previously reported (Mujumdar et al. (1993), Cyanine Dye Labeling Reagents: Sulfoindocyanine Succinimidyl Esters, *Bioconjugate Chemistry*, 4, 105-111).

Chemical conjugation of G5 PAMAM dendrimers with Cy5, dibenzocyclooctyne (DBCO) amine and acetyl groups was carried out by the following procedure: G5 PAMAM dendrimer (100 mg 5% MeOH solution, 5 mg Dendrimer, 0.173 µmol) was diluted with methanol (1 mL). To this solution, Cy5-NHS (1.37 mg, 1.73 gmol) or Cy3-NHS (1.33 mg, 1.73 µmol) in DMF (50 µL) was added and stirred for 30 min at room temperature, and the solution was then transferred into a 10K MWCO Amicon membrane filter (15 mL capacity) and centrifuged (1500 rpm) multiple times until no free unreacted Cy5 dye was detected in the filtrate. After rinsing the reaction media, DBCO NHS ester (1.20 mg, 1.70 µmol) in 50 µL DMF was added to the Cy5-conjugated dendrimer (1 mL MeOH) solution. Covalent attachment of DBCO proceeded using the same protocol as described for Cy5 attachment. The Cy5 and DBCO-conjugated G5 PAMAM dendrimer sample was washed, diluted into 1 mL MeOH, and acetic acid NHS ester (25 µmol, 4.00 mg) in 100 µL DMF was added and stirred for 2 hours at room temperature. The dendrimer sample was purified by centrifugation using 10K MW cutoff Amicon membrane filter (1500 rpm). The G5 PAMAM dendrimer conjugated with Cy5, DBCO and acetyl groups was stored in methanol as a stock solution. G6 PAMAM dendrimers were synthesized using an analogous reaction scheme as for G5 PAMAM dendrimers. MALDI-TOF mass analysis was performed using a Voyager-DE STR mass spectrometer with 2,5-dihydroxybenzoic acid (DHB) as a matrix.

Fluorescence Imaging and Analysis:

Fluorescence Microscopy.

Single organic dyes and FDN molecules were imaged using an inverted microscope (Olympus IX71) equipped for objective-type total internal reflection fluorescence microscopy (TIRF-M) using a 100× oil-immersion objective (NA=1.40) and an electron multiplied charge coupled device (EMCCD) camera (Andor iXon DU-897) (Selvin and Ha (2008), *Single-Molecule Techniques: A Laboratory Manual*: Cold Spring Harbor Laboratory Press). Cy5-FDN and single Cy5 molecules were illuminated using a CW solid state laser (Spectra Physics, Excelsior, 638 nm, 35 mW) with laser excitation powers ranging between 0.7-14 mW. Cy3-FDN. Single Cy3 molecules and Cy3-FDNs were illuminated using a CW solid state laser (Crystal Laser, 50 mW, 532 nm, GCL-050-L, low noise CW DPSS laser). Successive images of single fluorophores were acquired using 30 ms, 100 ms or 250 ms exposure times. For Cy3 imaging experiments, the detection path was split by a dichroic mirror (FF518-Di01-25×36, Semrock, Rochester, N.Y.) and wavelength selection was implemented using an long pass filter (HQ545LP). For Cy5 imaging experiments, the detection path was split by a dichroic mirror (FF650-Di01-25×36, Semrock, Rochester, N.Y.) and wavelength selection was implemented using a bandpass filter (HQ700/75m) and a long pass filter (HQ665LP), as described by Selvin and Ha (2008), vide supra.

Surface Immobilization Via PEG/PEG-Biotin.

For single molecule experiments involving either single dye molecules (Cy5 or Cy3) or FDNs (Cy5-FDNs or Cy3-FDNs), all species (single dyes and dendritic probes) were specifically linked to PEGylated surfaces using a similar copper-free click chemistry attachment scheme, as described here. First, PEGylated glass slides were prepared using a mixture of biotin-PEG-NHS ester (MW 3500 g/mol) and mPEG-NHS ester (MW 5000 g/mol) (Selvin and Ha (2008), *Single-Molecule Techniques: A Laboratory Manual*: Cold Spring Harbor Laboratory Press). PEGylated glass coverslips were then rinsed with TE50 binding buffer (10 mM Tris/Tris HCl at pH 8.0, 50 mM NaCl, 1.0 mM EDTA), followed by incubation with NeutrAvidin (1 mg/mL) to facilitate covalent coupling of fluorescent dendritic nanoprobes (FDNs) to glass coverslip surfaces. Next, 1 µM of biotin-azide was incubated with the NeutraAvidin treated surfaces, followed by a 5 minute incubation with FDNs (50 pM). In this way, FDNs are linked to glass coverslip surfaces using copper-free click chemistry to surface-bound azide groups, which were immobilized via avidin-biotin linkages. Finally, glass coverslips were rinsed with copious amounts of TE50 buffer. Here, single-channel slides glass were rinsed ~4× to remove unbound fluorescent probe on the surface. The coverslip was used to fabricate a simple flow cell formed by double-sided tape affixed onto a clean glass slide (Fisher Scientific). After rinsing, the coverslip/flow cell assembly was imaged with total internal reflection fluorescence microscopy (TIRF-M).

Imaging, Analysis and Spectrophotometry.

Single molecule imaging was performed using TE50 imaging buffer (10 mM Tris/Tris HCl at pH 8.0, 50 mM NaCl, 1.0 mM EDTA) in the presence of an oxygen scavenging system to minimize photobleaching, which consisted of glucose oxidase, catalase and glucose (0.3 mg/ml, 0.3 mg/ml, 0.8 w/v, respectively). Image analysis was performed using Image J and Matlab (Mathworks, R2010a). The Time Series Analyzer (Version 2.0) plug-in in Image J was used to track fluorescent probes, and subsequent analysis was performed with Microsoft Excel and Matlab. Matlab was used to fit modified two-dimensional (2D) Gaussian functions and to track the photobleaching lifetimes for fluorescent tags. For determination of localization precision and spatial resolution, a custom IDL code and a custom Matlab code was used. For data acquisition, the linear EMCCD camera response was verified using fluorescence intensity measurements of single fluorophores. A linear detection response with increasing probe brightness was determined. Where indicated, images were corrected by subtracting background values. OriginPro 8.5 was used for subsequent data analysis and plots. Bulk scale, ensemble-averaged fluorescence measurements were performed using a Varian Cary Eclipse fluorescence spectrophotometer (Agilent Technologies) at 610 nm excitation wavelength. Absorption spectra were acquired using Nanodrop UV-Vis spectrophotometer (Thermo Scientific).

Chemical Analysis of Dendrimer Conjugates.

A summary of MALDI-TOF mass spectrometric measurement of G5 and G6 PAMAM (ethylenediamine core) dendrimers modified with various surface-bound groups (e.g., see FIG. 1a) is presented in Tables 1-4. In the tables, Mn corresponds to the polymer number average molecular weight, Mw refers to the polymer weight average molecular weight, and PDI refers to the polydispersity index (PDI=Mw/Mn). The Substituent MW corresponds to the molecular weight of the substituents linked to dendrimers, including Cy5 dye molecules, DBCO, or acetyl (Ac) groups. The number of attachments corresponds to the number of substituent moieties linked to the dendrimer at each attachment step. For example, in Table 1, each G5 dendrimer contains approximately 7.8 Cy5 dye molecules in its surface, on average, as determined by MALDI-TOF.

TABLE 1

Summary of Dendritic Nanoprobe Samples.

|  | G5-REF | G5-Cy5 | G5-Cy5-DBCO | G5-Cy5-DBCO-Ac |
|---|---|---|---|---|
| Mn | 23420.7 | 28425.1 | 34446.6 | 37652.6 |
| Mw | 23989.3 | 29134.9 | 35253.4 | 38393.0 |
| PDI | 1.02 | 1.02 | 1.02 | 1.02 |
| Substituent MW | — | 638.8 | 620.7 | 42.0 |
| # of attachments | — | ~7.8 | 9.7 | 76 |

G5 PAMAM dendrimers were modified with ~0.8 surface-bound Cy5 dyes, dibenzocyclooctyne (DBCO) and acetyl groups (Table 2). The number of attachments corresponds, to the number of substituent moieties linked to the dendrimer at each attachment step (e.g., each G5 dendrimer contains approximately 0.8 Cy5 dye molecules, on average, as determined by MALDI-TOF).

TABLE 2

Summary of Dendritic Nanoprobe Samples.

|  | G5-REF | G5-Cy5 | G5-Cy5 DBCO | G5-Cy5 DBCO-Ac |
|---|---|---|---|---|
| Mn | 23856.23 | 24386.16 | 29781.48 | 31988.03 |
| Mw | 24418.27 | 24913.41 | 30500.46 | 32601.93 |
| PDI | 1.02 | 1.02 | 1.02 | 1.02 |
| Substituent MW | — | 638.8 | 620.7 | 42.0 |
| # of attachments | — | ~0.8 | ~7 | 52 |

G6 PAMAM dendrimers were modified with ~14 surface-bound Cy5 dyes, biotin, dibenzocyclooctyne (DBCO) and acetyl groups. The number of attachments corresponds to the number of substituent moieties linked to the dendrimer at each attachment step (e.g., each G6 dendrimer contains approximately 14 Cy5 dye molecules, on average, as determined by MALDI-TOF).

TABLE 3

Summary of Dendritic Nanoprobe Samples.

|  | G6-REF | G6-Cy5 | G6-Cy5-biotin | G6-Cy5-biotin-DBCO | G6-Cy5-biotin-DBCO-Ac |
|---|---|---|---|---|---|
| Mn | 44661 | 53513 | 58996 | 64353 | 69885 |
| Mw | 46976 | 54742 | 60176 | 65839 | 71375 |
| PDI | 1.02 | 1.02 | 1.02 | 1.02 | 1.02 |
| Substituent MW | — | 638.8 | 474.7 | 620.7 | 42.0 |
| # of attachments | — | ~14 | ~12 | ~9 | ~132 |

G5 PAMAM dendrimers were modified with ~7.7 surface-bound Cy3 dyes. The number of attachments corresponds to the number of substituent moieties linked to the dendrimer at each attachment step (e.g., each G5 dendrimer contains approximately 7.7 Cy3 dye molecules, on average, as determined by MALDI-TOF).

TABLE 4

Summary of Dendritic Nanoprobe Samples.

|  | G5-REF | G5-Cy3 |
|---|---|---|
| Mn | 23856.23 | 28563.63 |
| Mw | 24418.27 | 29273.45 |
| PDI | 1.02 | 1.02 |
| Substituent MW | — | 612 |
| # of attachments | — | ~7.7 |

Dye-conjugated dendrimer samples were analyzed by MALDI-TOF mass spectrometry, and the average number of acetyl groups on the G5 dendrimer surface was found to be 76-80. Further functionalization of the G5 dendrimer surface was generally not possible due to steric hindrance, and the electrostatic interactions between the Cy5 sulfonate and dendrimer terminal $NH_3^+$ groups appear to hinder complete acetylation of the terminal amines. All Cy5 molecules are located within a 5-8 nm distance on the dendrimer surface.

Following synthesis and chemical analysis, the photophysical properties of dye-conjugated dendrimers were characterized using SMFM. First, dye-conjugated dendrimers were immobilized on a glass coverslip surface using specific chemical linkages (FIG. 1b). PEGylated coverslips containing a mixture of PEG/PEG-biotin were treated with NeutrAvidin, rinsed thoroughly, and incubated with a biotin-azide linker. Next, the G5-Cy5-DBCO dendrimers were incubated with the functionalized coverslips at a Cy5-dendrimer concentration of 30-40 pM, thereby surface-immobilizing dendrimer molecules via a "copper-free click" reaction.[18] Overall, this approach yields single isolated dye-conjugated dendrimers linked specifically to coverslip surfaces through biotin-avidin interaction, which is a common strategy for biomolecule immobilization to PEGylated surfaces for single molecule fluorescence microscopy.[1,5] Single dendrimer molecules were imaged in the presence of an oxygen scavenger system using total internal reflection fluorescence microscopy (see Table 1 above).

Using SMFM, the fluorescence intensity of individual dye-conjugated dendrimer molecules was tracked until photobleaching. Dye-conjugated dendrimers are bright, resulting from increased fluorescence emission from multiple dyes. The fluorescence intensity trajectory of a single Cy5-dendrimer is shown in FIG. 1c, which reveals a multi-step photobleaching event, arising from successive, step-wise photobleaching of individual Cy5 dyes.

Figure 2:
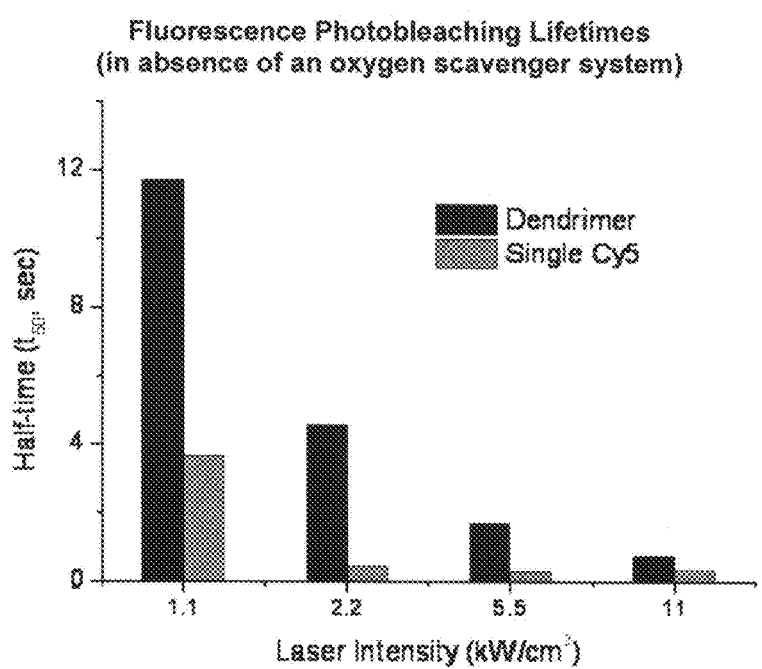
FIG. 2. Fluorescence Photobleaching Lifetimes (in absence of an oxygen scavenger system). Average time to photobleach 50% of the initial population of fluorophores (defined as half-time) as a function of excitation intensity for single dye-conjugated dendrimer molecules and single Cy5 molecules in the absence of an oxygen scavenger system. Overall, the general response is similar to photobleaching lifetimes with oxygen scavengers; however, the timescale for photobleaching is much shorter in the absence of oxygen scavengers. TE50 buffer was used as an imaging buffer.

FIG. 2 shows photobleaching lifetimes for dye-conjugated dendrimer molecules and single dye molecules. Photobleaching lifetimes are calculated by tracking individual fluorescence intensity trajectories from single G5-Cy5-DBCO dendrimers and recording the time required for fluorescent probes to bleach to a dark state under constant excitation. FIG. 3a shows the active fraction of fluorescent molecules (dendrimers or single dyes) as a function of time, averaged over a ~1000 molecule ensemble. Unexpectedly, Cy5-conjugated dendrimer molecules exhibit extremely long photobleaching lifetimes compared to single Cy5 dye molecules. Photobleaching lifetimes for single dendrimer molecules as a function of laser excitation intensity were also characterized (FIG. 3b).

The fluorescence half-time is defined as the time required for 50% of the initial population to bleach to a dark state. In all cases, the photobleaching lifetimes of dye-conjugated dendrimers far exceed the lifetimes of single dyes (factor of ~6-10). At low excitation intensities typical for SMFM, half of the Cy5-dendrimer population remains fluorescent in excess of ~300 seconds (5 minutes) under constant illumination, whereas half of the single Cy5 dye population photobleaches within ~50 seconds. In these experiments, dendrimer molecules and single dye molecules were specifically linked to PEGylated surfaces using a similar copper-free click chemistry attachment scheme.

Overall, the active fraction of Cy5-dendrimers displayed a remarkably linear time-dependent decay response, whereas the non-photobleached fraction of single dyes fit to a single exponential decay. In this way, Cy5-dendrimers avoid the rapid initial transient decay typically observed using single dyes and remain bright and photoactive for longer periods. Therefore, dye-conjugated dendrimers are capable of providing extended observation times for SMFM experiments, which may be useful for assaying biological dynamics over longer periods of time.

Figure 4:
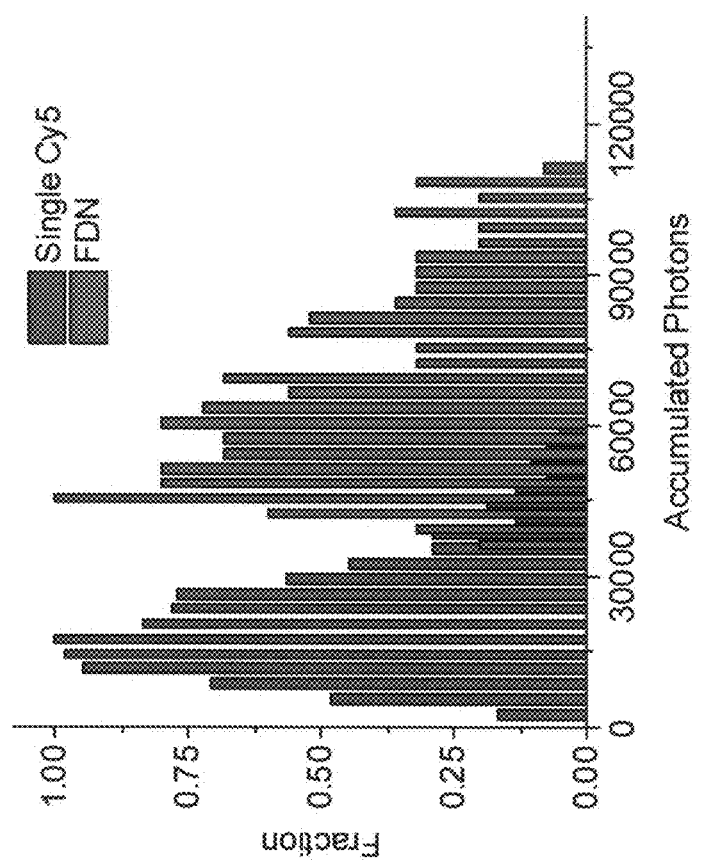
FIG. 4. Histogram of the number of collected photons for Cy5-FDNs (G5 with ~8 Cy5 dyes) and single Cy5 dyes imaged using the same excitation conditions. For Cy5-FDNs and single Cy5 dyes, the total number of photons was determined from sampling >800 single molecules, and the data were corrected for the background signal.

The fluorescence intensity of single dye-conjugated dendrimer molecules was also measured using SMFM. In FIG. 4, fluorescence intensities between single Cy5 dye molecules and single dye-conjugated dendrimers were compared. As shown in FIG. 4, the fluorescence intensity of Cy5-dendrimers was higher compared to single dye molecules.

Figure 5:
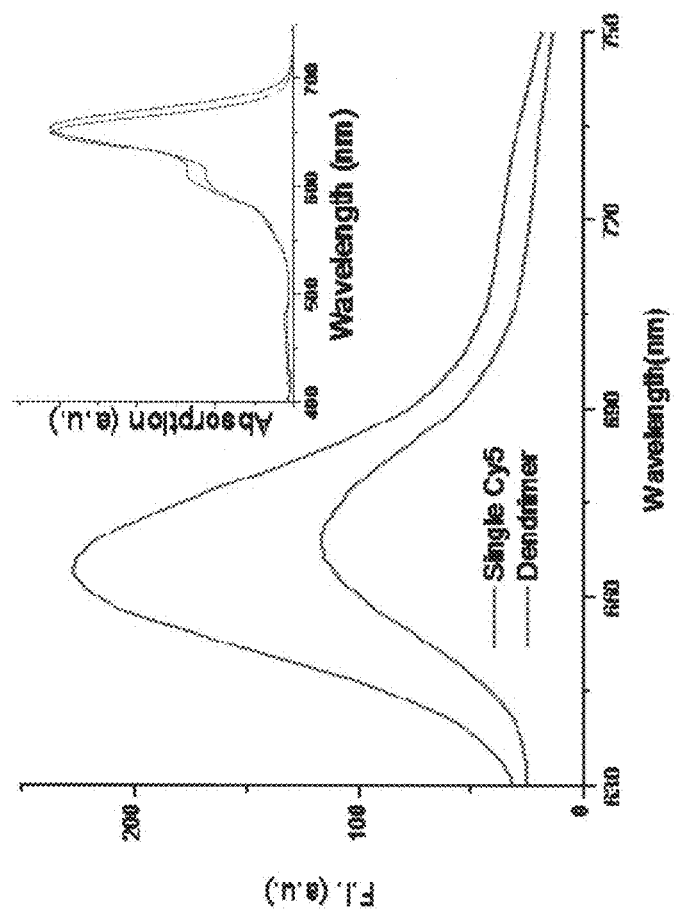
FIG. 5. Comparison of bulk fluorescence intensity from Cy5-dendrimers and Cy5 dyes: ensemble average fluorescence intensities for Cy5-dendrimers and Cy5 molecules. The fluorescence intensity of single Cy5 molecules and Cy5-dendrimers was measured at concentrations having equal absorption. The dye absorption spectra are shown in the inset.

Although Cy5-FDNs are brighter than single organic dyes, the increase in probe brightness does not scale linearly with the average number of conjugated dyes per Cy5-FDN molecule. For example, Cy5-FDNs based on G5 PAMAM dendrimers show a ~2-5× increase in the number of collected photons relative to single Cy5 dyes, which does not match the average number Cy5 dyes per probe (~8) determined by MALDI-TOF mass spectrometry analysis. To investigate fluorescence emission intensities for Cy5-FDNs, the bulk fluorescence emission for Cy5-FDN samples and Cy5 dye samples was measured at equivalent dye concentrations based on equal absorption (FIG. 5). Bulk fluorescence measurements showed that Cy5-FDN fluorescence emission was ~45% less intense (per dye molecule) compared to free Cy5 dye samples, which is in good agreement with single molecule fluorescence data. If individual dye molecules on dendrimer scaffolds are independent, non-interacting fluorophores, then photobleaching lifetimes are not expected to increase compared to single dye molecules, and the fluorescence emission intensity of single Cy5-FDNs would scale linearly with the number of dye molecules conjugated to dendrimer surfaces. Based on these results, Cy5 dyes likely interact through collective photophysical effects on macromolecular scaffolds.

The photophysical properties of multichromophoric systems have been studied previously using natural light harvesting complexes[19] and aromatic dendrimers bearing perylene dyes.[20] Collective effects in multichromophoric systems can arise due to several photophysical mechanisms. Strong excitonic coupling can occur for dyes located in close proximity (<1 nm), which results in energy delocalization and a new quantum system. Strong coupling results in splitting of the excited electronic state with new selection rules for electronic transitions, thereby yielding H-dimers[21] with blue-shifted absorption and fluorescence quenching, or J-dimers with red-shifted absorption and enhanced fluorescence emission.[22,23] Weak excitonic coupling can occur for larger interchromophoric spacings (~1-2 nm), resulting in reduced fluorescence emission but no observable change in absorption spectra.[22]

Chemically identical fluorescent dye molecules can interact when located in close proximity, thereby resulting in collective interactions between multiple fluorophores.[20,21,22,24] For Cy5-FDNs based on G5 dendrimers conjugated with 8 dyes, the maximum interchromophoric spacing between two individual dyes on a single Cy5-FDN is ~3-4 nm (based on geometrical considerations), which allows for the possibility of strong or weak excitonic coupling. However, strong excitonic coupling is unlikely, because the bulk absorption spectrum for FDN samples is neither blue nor red-shifted compared to free Cy5 dye (FIG. 5) or to FDNs labeled with only ~1 Cy5 dye per probe. On the other hand, weak excitonic coupling is supported by single molecule experiments. Single molecule fluorescence intensity traces show that a sub-population of Cy5-FDNs exhibits structured, stepwise photobleaching behavior (FIG. 1c), whereas a separate sub-population shows broad, unstructured fluorescence intensities. Unstructured fluorescence intensity traces have been attributed to weak excitonic coupling interactions for aromatic dendrimers labeled with multiple dyes,[20] which may explain the reduced fluorescence emission observed for Cy5-FDNs (FIG. 5). Moreover, weak coupling interactions could also explain the non-exponential photobleaching behavior for Cy5-FDNs shown in FIG. 3a. To explore this phenomenon further, Cy5-FDNs containing an average of ~1 Cy5 dye on G5 PAMAM scaffolds were synthesized. It was observed that the photobleaching half-time for Cy5-FDNs containing ~1 Cy5 dye was similar to the photobleaching half-time of single (free) Cy5 dyes, which indicates that putative interactions between Cy5 molecules and dendritic scaffolds do not give rise to altered photophysical effects such as enhanced photostability. Based on these results, the extended photobleaching lifetimes can be attributed to weak coupling interactions between dye molecules on dendritic nanoprobes.

Fluorescent nanoprobes containing multiple dye molecules can also enhance localization precision. The point spread function (PSF) was calculated using two-dimensional (2D) Gaussian fitting to localize fluorescent dendrimers with sub-diffraction accuracy,[25] and the precision of centroid determination for single Cy5-dendrimers and single Cy5 molecules was determined (FIG. 4). Overall, the localization precision for Cy5-dendrimers was enhanced compared to single Cy5 dyes due to increased brightness. Because Cy5-dendrimers and single Cy5 molecules yield diffraction limited images, the FWHM for the 2D Gaussian fit should be similar. However, brighter fluorescent tags can yield smaller FWHM,[26] and a modest decrease in the FWHM for Cy5-dendrimers containing multiple dyes was observed (FIG. 7).

Localization Precision for Single Cy5-Dendrimers and Single Cy5 Dyes.

The images of Cy5-dendrimers and single Cy5 molecules were analyzed by a custom IDL code (IDL 7.1, ITT VIS). A 10×10 pixel diffraction limited image of each fluorophore was fitted to an asymmetric 2-D Gaussian function to obtain its position (x,y) and error ($\sigma_x$, $\sigma_y$). The error is a measure of the localization precision as described by Thompson and coworkers (Precise Nanometer Localization Analysis for Individual Fluorescent Probes, *Biophysical Journal* (2002) 82, 2775-2783):

$$\sigma_{\mu i} = \sqrt{\frac{s_i^2}{N} + \frac{\frac{a^2}{12}}{N} + \frac{8\pi s_i^4 b^2}{a^2 N^2}}$$

where $\sigma_{\mu_i}$ is the localization precision in each lateral direction (x or y), $s_i$ is the standard deviation of the Gaussian fit (along x or y), N is the total number of collected photons, a is the effective pixel size (160 nm at 100× magnification with 16×16 μm camera pixels) and b is the standard deviation of the background (including background fluorescence noise and detector noise). In this expression, the first term arises due to photon noise, the second term arises from the effect of finite pixel size of the detector, and the last term arises due to background.

Figure 6:
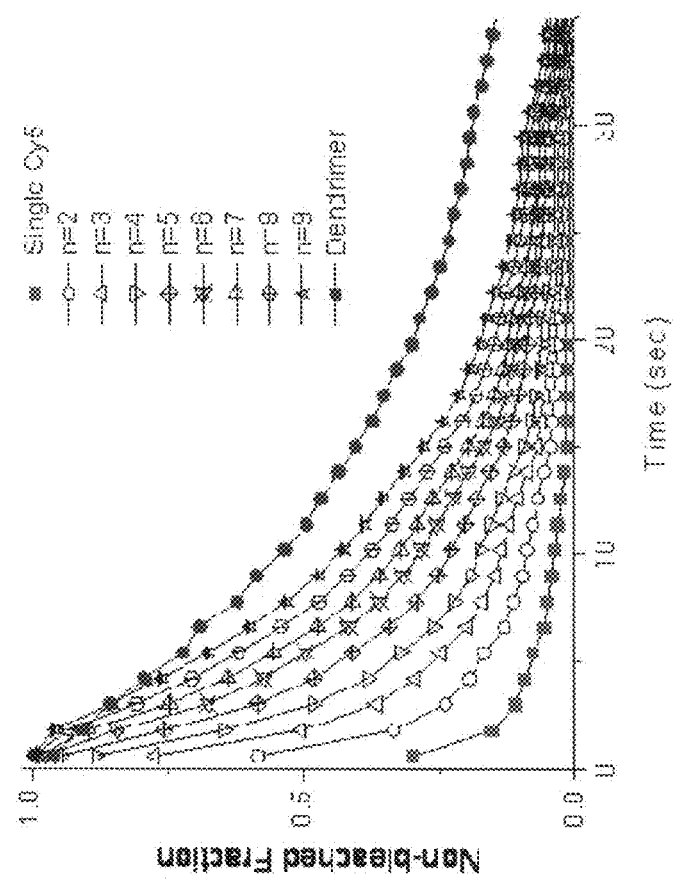
FIG. 6. Testing self-quenching for enhanced photobleaching lifetimes. Experimental results and calculation of fluorescence photobleaching lifetimes for Cy5-dendrimers using an excitation intensity of 21.9 kW/cm² (14 mW). Experimental data is shown for single Cy5 (red square) and Cy5-dendrimer (blue circle) photobleaching lifetimes. Additional curves (central curves) show the results of calculations, assuming that individual dyes on dendrimer molecules act independently. The summed response of photobleaching lifetime for increasing number of dyes on a single hypothetical dendrimer does not match the experimental data for Cy5-dendrimers containing multiple dye molecules.

This example therefore provides a scheme for synthesizing dye-conjugated PAMAM dendrimers as fluorescent nanoimaging probes. Single molecule fluorescence measurements reveal that dye-conjugated dendrimers exhibit extended photobleaching lifetimes compared to single dye molecules (see FIG. 6). Dendrimers can be used as a molecular scaffold to effectively "package" multiple dye molecules into a single, nanometer-sized macromolecule, thereby making them viable candidates for a new class of fluorescent probes. Dye-conjugated dendrimers can also further increase the resolution of super-resolution microscopy techniques due to increased numbers of photons collected from single dendrimer molecules.[10,27] In addition, dye-conjugated dendrimers can be used to extend the photobleaching lifetimes for FRET measurements, thereby yielding improvements in dynamic assays. Multi-color dye-conjugated dendrimers can also enable spectral barcoding and multiplexing applications using molecular-based tags.

Example 2

Photoswitchable Dye-Conjugated Dendrimers

Photoswitchable dye-conjugated dendrimers have been prepared and evaluated. Dendrimers were synthesized to contain both Cy3 and Cy5 dyes, and it has been directly demonstrated that the Cy5 dyes can be switched on by a transient pulse of green light (532 nm), which is absorbed by Cy3. This mechanism is similar to the photoswitching mechanism used for *single* molecules of Cy3/Cy5 currently used in STORM super-resolution microscopy. However, dye-conjugated dendrimers are brighter and contain more dyes, which properties enhance the precision of centroid determination and results in sharper images. Data showing photoswitching events is shown in FIGS. 8 and 9.

Figure 8:
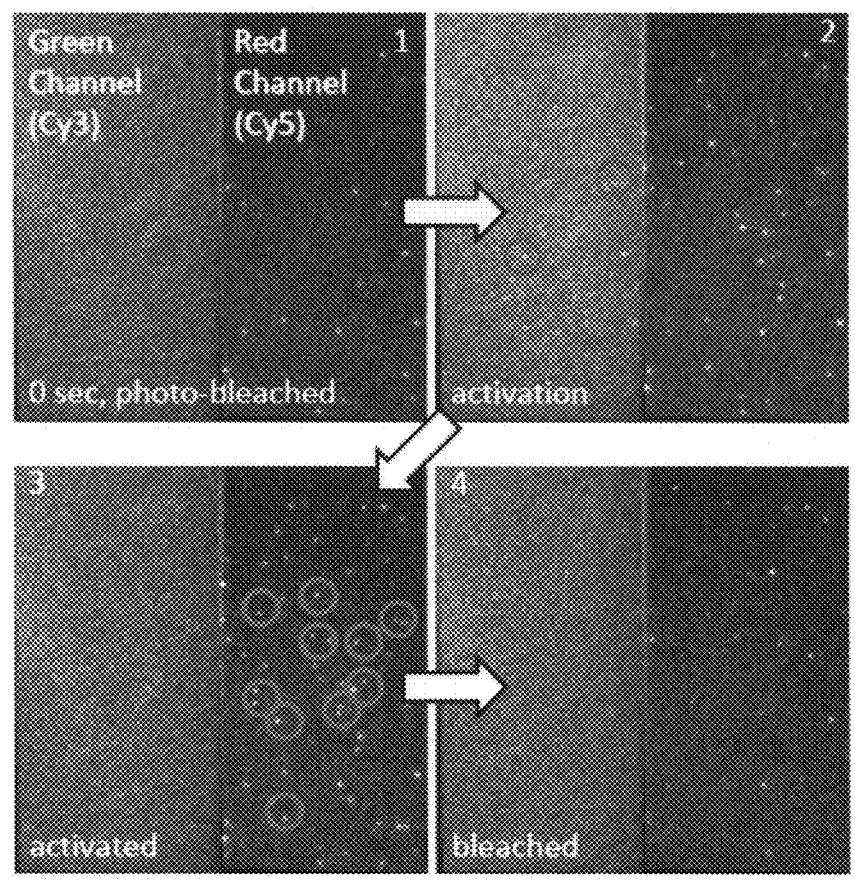
FIG. 8. Panels 1-4 showing a photoswitching event using single dendrimers conjugated with Cy3 and Cy5 dyes.
Figure 9:
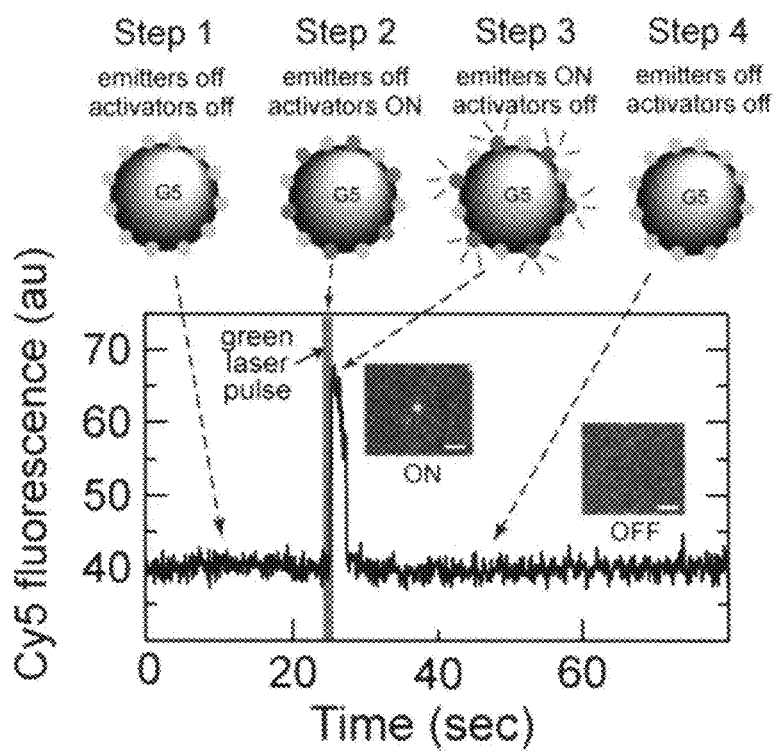
FIG. 9. Photoswitchable FDN probes. (a) A photoswitching event for a single FDN probe is shown with a schematic illustration of the process. In Step 1, the emitter dyes (Cy5) are fully bleached to a dark state. In Step 2, a brief laser pulse (~0.5 second) of green light (532 nm) is applied, which transiently illuminates the activator dyes (Cy3). In turn, the Cy3 dyes "switch on" the Cy5 dyes in Step 3. It should be noted that multiple Cy5 dyes "switch on" during one of these photoswitching events, and the entire nanostructure of the FDN probe becomes bright, with the total brightness much greater than that of a single Cy5 dye. The emitter dyes (Cy5) are imaged until reversibly photobleaching again in Step 4. (b) The photoswitching process for FDN probes is reversible in the presence of thiols in solution. The trajectory shows the fluorescence intensity for a single FDN probe reversibly cycled between bright/dark states, as explained in the process in part (a). (c) The photoswitching process for FDN probes is reversible in the absence of thiols in solution. The trajectory shows the fluorescence intensity for a single FDN probe reversibly cycled between bright/dark states, as explained in the process in part (a).
Figure 9:
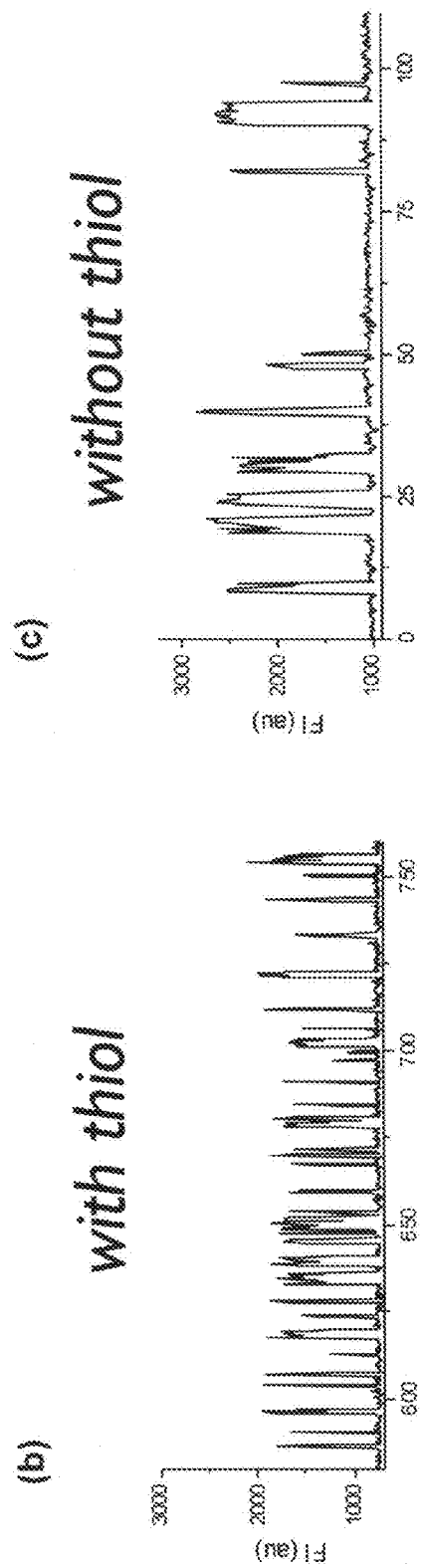

Panels 1-4 of FIG. 8 show a photoswitching event using single dendrimers conjugated with Cy3 and Cy5 dyes at a ratio of 2:7 (Cy3:Cy5). Dendrimers are specifically linked to a PEGylated coverslip via biotin-Neutravidin linkage.

Panel 1. Bleaching (time 0): The majority of Cy5 dyes are photobleached (although some are remain active and not fully bleached). The red laser was on to photobleach Cy5 molecules.

Panel 2. Photoactivation: The green laser is turned on for ~0.5 seconds. The green circles in panel 2 show fluorescence emission from several Cy3 molecules.

Panel 3. Activated Cy5: Immediately after the activation step, dark state Cy5 molecules are photoswitched to the "on" state. The red circles show the activated Cy5.

Panel 4. Bleaching: After some time, re-activated Cy5 molecules return to a dark state again, by strong red laser illumination. This process is stochastic and may be repeated.

At the start of this experiment (panel 1), the red laser (632 nm) is on, and most of the Cy5 dyes are therefore bleached. At panel 2, a green laser (532 nm) is turned on for approximately 0.5 seconds, and is then turned off. The green laser pulse activates Cy5 molecules, and several Cy5 molecules "switch" on (panel 3), potentially mediated by a photochemical process due to transient Cy3 emission. Re-activated Cy5 molecules then return to a dark state (panel 4), by strong red laser illumination.

FIG. 9 illustrates fluorescence trajectories of photoswitching events on single dendrimers. Individual fluorescence intensity trajectories for single dendrimers are shown (Cy5 emission). Y-axis shows the fluorescence intensity (a.u.) for Cy5 dyes. The green laser was turned on at the green vertical line through the left and right sets of graphs. In this example, the dendrimers contain approximately 5 molecules of Cy5 (red) and 2 molecules of Cy3 (green).

Figure 10:
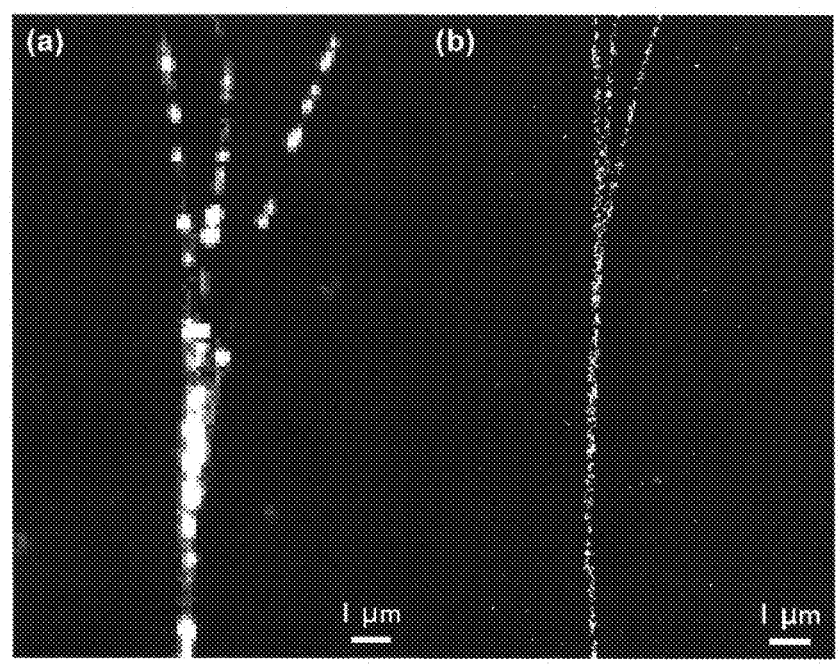
FIG. 10. Super-resolution images of microtubules acquired using photoswitchable dye-conjugated dendrimer probes. (a) Diffraction-limited image of microtubules obtained using dye-conjugated dendrimers, and (b) super-resolution image of microtubules obtained by image reconstruction using photoswitchable dendrimer probes.

Super-resolution images of microtubules acquired using photoswitchable dye-conjugated dendrimer probes (FIG. 10). (a) A diffraction-limited image of microtubules obtained using dye-conjugated dendrimers is shown in FIG. 10a, while a super-resolution image of microtubules obtained by image reconstruction using photoswitchable dendrimer probes is shown in FIG. 10b.

Photo switchable dye-conjugated dendrimers are therefore a new class of nanoprobes (fluorescent tags) for super-resolution microscopy.

Example 3

Combinatorial Dye Conjugation

Figure 11:
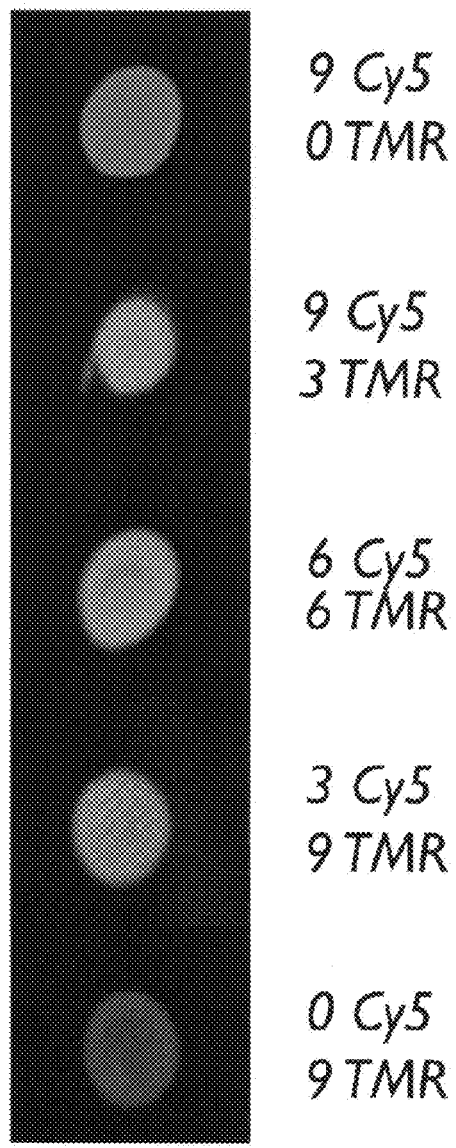
FIG. 11. Combinatorial dye conjugation resulting in 5 distinct spectral wavelength signatures (mixed colors) using only 2 dyes (Cy5 and TMR). To create the color images, 535 nm and 635 nm laser were used for excitation and 565 nm and 665 nm filters were used to collect emission data for corresponding TMR and Cy5. The collected emission intensities were summed to create the pseudo-color images.

Multi-dye conjugated dendrimers were prepared to provide distinct spectral wavelength signatures as shown in FIG. 11, which illustrates combinatorial dye conjugation resulting in 5 distinct spectral wavelength signatures (mixed colors) using only 2 dyes (Cy5 and TMR). The methods for preparing the multi-dye conjugated dendrimers is as described above for generating single dye dendrimers, except that two color dyes are added in stoichiometric proportion at the target labeling ratio.

The procedural details are as follows. To 5 Eppendorf tubes, each tube containing a G5 PAMAM dendrimer (1 mg) in methanol 200 µL, were separately added (1) TMR-NHS (0.17 mg) in 10 µL DMF, (2) TMR-NHS (0.17 mg) in 10 µL DMF and Cy5-NHS (0.08 mg) in 10 µL DMF, (3) TMR-NHS (0.11 mg) in 10 µL DMF and Cy5-NHS (0.17 mg) in DMF, (4) TMR-NHS (0.06 mg) in 10 µL DMF and Cy5-NHS (0.25 mg) in DMF, and (5) Cy5-NHS (0.25 mg), and were stirred for 30 minutes at room temperature (~23° C.). This solution was transferred into 0.5 mL 10K cut off centricon membrane filter and was centrifuged multiple times until the no further color passed through the membrane filter at 5000 g force. The different ratios of TMR and/or Cy5 labeled G5s were printed on the glass slide and scanned with dual lasers (535 nm and 635 nm excitation) equipped with 565 nm and 665 nm emission filters. The pseudo color was created by mixing the emission intensities obtained from the emission filter (Table 5).

TABLE 5

Generations of Composite Color Using Two Dyes in Different Ratios.

| | Dye | | Composite |
|---|---|---|---|
| | TMR (Tetramethyl Rhodamine) Color | Cy5 | color (Pseudo |
| | Green | Red | color) |
| Ratio | 6 | 6 | Coral |
| | 9 | 3 | Yellow |
| | 9 | 0 | Green |
| | 0 | 9 | Red |
| | 3 | 9 | Dark Orange |

Example 4

Single Molecule Protein Pull Down Assay

Figure 12:
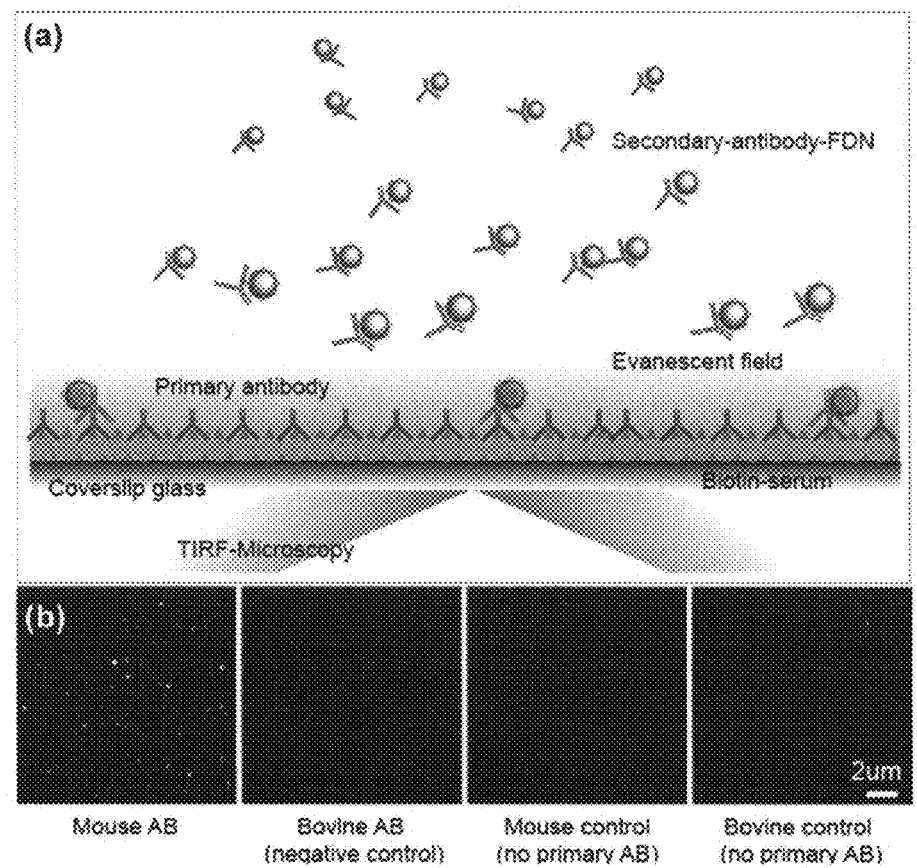
FIG. 12. Single molecule protein pull down assay (SiM-Pull) using Cy5-FDNs as fluorescent probes. (a) Schematic of single molecule experimental scheme. Anti-biotin primary antibody incubated with surfaces treated with biotinylated serum, which minimizes non-specific protein interactions. Next, Cy5-FDN conjugated secondary antibody targeting mouse IgG and bovine IgG was incubated with primary antibody-treated surfaces. (b) Single molecule images obtained using the protein pull down assay, which clearly show high degrees of specific protein capture and low amounts of non-specific interactions. In this experiment, single molecule images were acquired using total internal reflection fluorescence microscopy. (c) The protein pull down assay was quantified by counting the average numbers of bound antibodies per field of view for target (mouse secondary) and negative control experiments.
Figure 12:
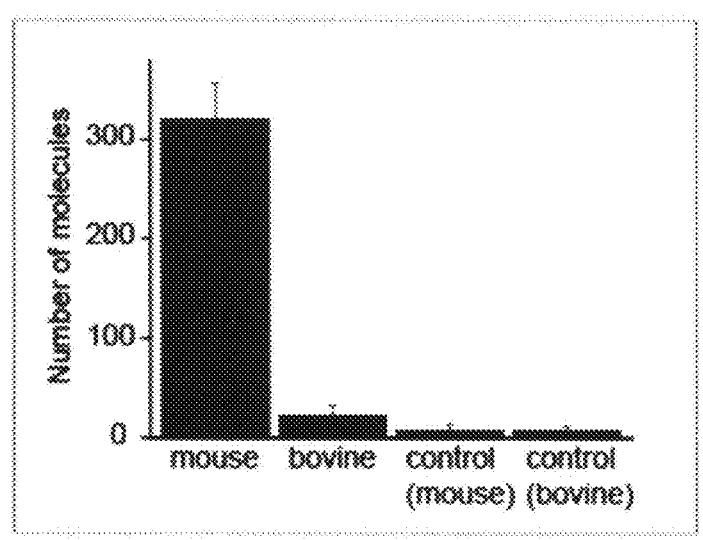

Beyond photophysical characterization, proof-of-principle applications of Cy5-FDNs to single molecule fluorescence imaging were demonstrated. In particular, Cy5-FDNs were used as fluorescent probes in a single molecule protein pull-down assay (SiMPull), which allows for target-specific capture of proteins at the single molecule level (FIG. 12).[28]

Single molecule protein pull down assays were conducted as previously described (Jain, A., et al., "Probing cellular protein complexes using single-molecule pull-down". Nature, 2011. 473(7348): p. 484-488). Anti-biotin primary antibody from mouse, whole IgG anti-mouse secondary antibody from goat and anti-bovine secondary antibody from goat was purchased from Jackson Immunolaboratory. Primary antibodies were reacted with Cy3 NHS-ester, and secondary antibodies were reacted with azide NHS-ester (Click Chemistry Tools, Macon, Ga.). Labeled antibody was purified by overnight dialysis (MW cutoff 3500 Da). Click chemistry reactions were performed at room temperature for two hours between multi-dye conjugates and azide-labeled antibodies. After reaction, products were purified with protein G column (Piercenet), and copious on-column washing was carried out to exclude unconjugated dye molecules. Protein labeling ratios were assayed by UV-Vis, which revealed labeling stoichiometries of 1.5:1 Cy3 dye:primary antibody and 0.4:1 FDN:secondary antibody. SDS-PAGE gels of purified and labeled antibodies were carried out and imaged using a STORM laser scanner (GE Healthcare) to verify conjugation of dyes and FDNs to antibodies.

Serum (goat) was used to block non-specific binding of secondary antibodies from goat. Glass slides and glass coverslips were cleaned with KOH and ethanol before the assay, as previously described. Next, biotin-labeled serum (5% w/v) was introduced into the microfluidic channels and washed ~5× with buffer. Anti-biotin primary antibody was applied and incubated for 5 minutes and washed ~3×. After rinsing, fluorophore-labeled secondary antibodies introduced and incubated for 5 minutes. Excess secondary antibodies were then rinsed from the channels (~10× rinsing cycle) to minimize non-specific binding. Finally, the secondary antibody solution was introduced with 5% w/v goat serum solution for blocking. Single molecule images were obtained using total internal reflection microscopy, and imaging was performed in the presence of an oxygen scavenger system, consisting of glucose oxidase, catalase and glucose (0.3 mg/ml, 0.3 mg/ml, 0.8 w/v, respectively) as previously described by Selvin and Ha (2008), vide supra.

Single molecule images were obtained using TIRF-M, as shown in the schematic of the experimental setup in FIG. 12a. First, mouse and bovine secondary antibodies were conjugated with Cy5-FDNs using copper-free click chemistry. Next, anti-biotin primary antibody (mouse) was immobilized on biotin-serum coated glass coverslip surfaces, followed by incubation of Cy5-FDN-secondary antibody (mouse or bovine) to allow for target-specific protein capture. FIG. 12b shows representative images from the single molecule pull-down assay, which clearly demonstrate highly specific protein capture as revealed by Cy5-FDN probes. The average number of target mouse Cy5-FDN-secondary antibodies in a field of view was 320±36 (mouse primary antibody), which far exceeds the number of surface-bound molecules in control experiments (bovine primary antibody, 7±7; no mouse primary antibody, 22±9; no bovine primary antibody, 7±4) (FIG. 12c).

These results are consistent with previous reports obtained using single molecule protein capture assays for antibodies labeled with single organic dyes.[28] In an additional set of experiments, two-color fluorescence co-localization between Cy3-primary antibodies and Cy5-FDN-secondary antibodies was used to directly demonstrate high fidelity protein capture between target proteins. Importantly, it was found that labeling secondary antibodies with dendritic nanoprobes neither hinders functionality nor significantly reduces specificity, which indicates that Cy5-FDNs can be used for target-specific protein labeling. In this way, Cy5-FDN probes offer the dual advantage of increased probe brightness with lower levels of protein modification, which is useful in maintaining functionality for antibody binding and protein capture experiments.

Figure 3:
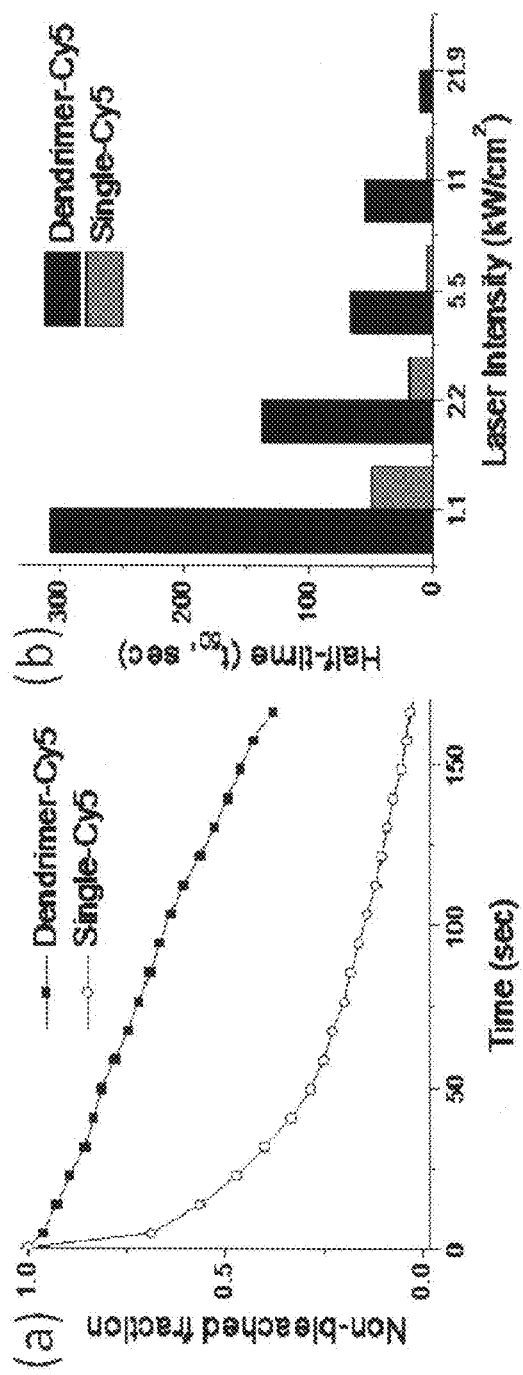
FIG. 3. Fluorescence photobleaching lifetimes for dye-conjugated dendrimer molecules and single dye molecules (in the presence of an oxygen scavenger system). (a) Fraction of active (non-bleached) fluorophores is shown for dendrimer molecules and single dye molecules. The active fraction was calculated by tracking the time before fluorophores bleached over a large ensemble of molecules. Samples were illuminated using 1.4 mW laser power (2.2 kW/cm$^2$ intensity). (b) Average time to photobleach 50% of the initial population of fluorophores (defined as half-time) as a function of laser power for dye-conjugated dendrimer molecules and single Cy5 dye molecules.
Figure 13:
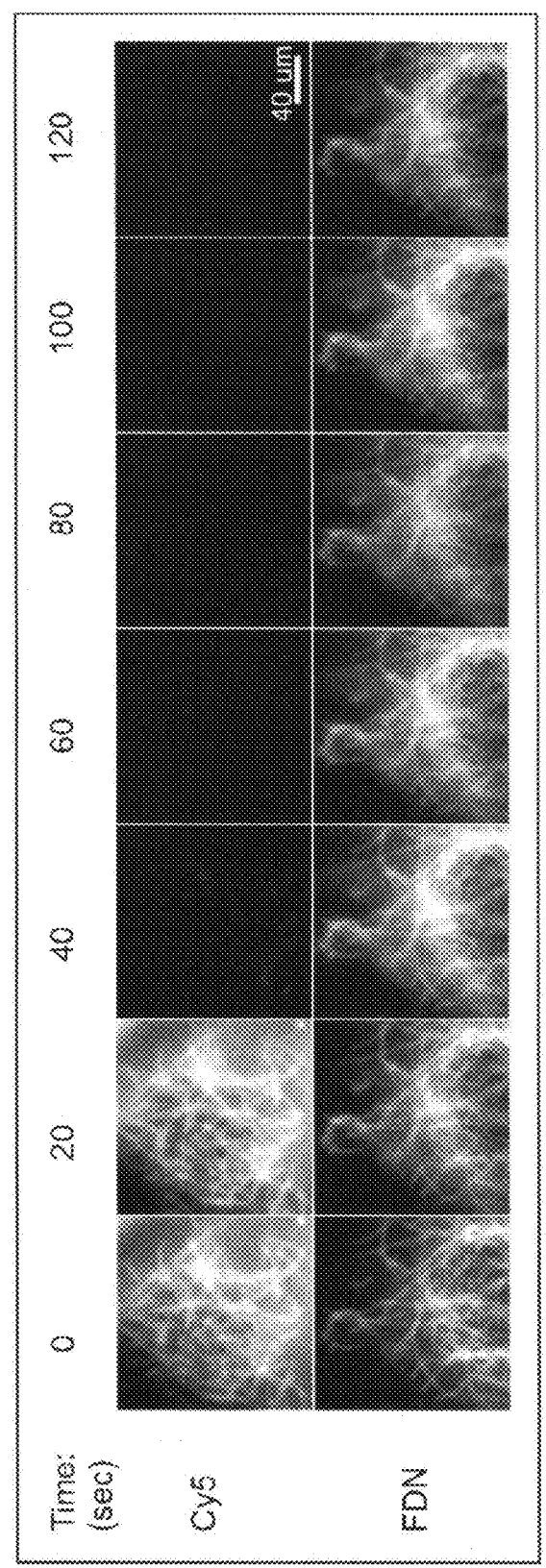
FIG. 13. Immunofluorescence imaging of cytoskeletal networks in mammalian cells using Cy5-FDN conjugated antibodies. Microtubules were immunostained with Cy5-FDN or Cy5-conjugated secondary antibodies. Time-lapse fluorescence microscopy images of immunostained microtubules show a markedly increased photostability for Cy5-FDN conjugated antibodies compared to Cy5-labeled antibodies. Images were obtained using the same excitation and imaging conditions (11 kW/cm², in the presence of glucose oxidase/catalase as an oxygen scavenging system). The concentration of secondary antibody was maintained constant in both experiments, and the labeling ratio was 0.4:1 and 1:1 probe:antibody for Cy5-FDN and Cy5 probes, respectively. Scale bar: 40 μm.

To further demonstrate proof-of-principle application of FDN probes for biological imaging, Cy5-FDNs was used for cell staining and immunofluorescence microscopy (FIG. 13). In this experiment, the microtubule cytoskeleton in mammalian cells (HEK293) was imaged by immunofluorescence microscopy using Cy5-FDN-conjugated antibodies. Microtubule networks in fixed HEK293 cells were labeled using a primary anti-alpha-tubulin antibody (clone AA13, mouse), followed by incubation with Cy5-FDN-conjugated secondary antibodies (anti-mouse). To facilitate labeling, secondary antibodies were modified with azide moieties via azide-NHS ester linkers, followed by direct conjugation to Cy5-FDNs by copper-free click chemistry. For labeling studies, the Cy5-FDN-to-antibody stoichiometry was adjusted to 0.4:1 (FDN:protein) to avoid conjugation of multiple Cy5-FDNs to secondary antibodies, whereas single Cy5 dyes were conjugated to secondary antibodies using a 0.9:1 (dye:protein) stoichiometry. FIG. 13 shows immunofluorescence images of microtubule networks obtained using both Cy5-FDN-conjugated and Cy5-conjugated secondary antibodies. Immunofluorescence images show that conventional, single organic dye-conjugated antibodies photobleach rapidly when obtained using moderate excitation intensity. However, immunofluorescence imaging using Cy5-FDN-conjugated secondary antibodies showed a vastly improved photostability, which agrees with photophysical characterization of Cy5-FDNs (FIG. 3). In all experiments, fixed cells were imaged in PBS solution containing an oxygen scavenger system (glucose oxidase/catalase). In general, secondary antibodies have a limited number of lysine or cysteine reactive sites to facilitate fluorescent probe conjugation, and labeling antibodies with FDNs utilizes fewer reactive sites given the same brightness increase relative to single organic dyes. Therefore, these results indicate that the quality of immunofluorescence images can be enhanced and acquired over longer periods of time using antibodies conjugated with Cy5-FDNs, which are brighter probes with enhanced photostability.

For the FDN probes characterized in this work, the emergent photophysical properties arise from the collective fluorescence emission from multiple fluorophores assembled onto single nanoscale probes. Multichromophoric systems are encountered in both natural and synthetic systems. In nature, the process of photosynthesis relies on collective interactions between multiple chromophores to capture photons at increased efficiencies. Although previous mechanistic studies have explored collective effects in systems such as light harvesting proteins and aromatic non-aqueous dendrimers,[29-32] our work aims to capitalize on the advantageous photophysical properties of multidye dendritic nanoconjugates to develop a new class of practical, versatile and functional molecular probes for fluorescence imaging.

In this work, dendritic nanoprobes as molecular-scale fluorescent probes for general fluorescence microscopy and single molecule fluorescence microscopy were described. The photophysical properties of FDNs were characterized, and the direct application of these probes to biological imaging experiments was demonstrate. Single molecule fluorescence measurements reveal that FDNs exhibit enhanced photostability and brightness compared to single organic dye molecules. In particular, PAMAM dendrimers function as molecular scaffolds to effectively "package" multiple dye molecules into single, nanometer-sized macromolecules, thereby generating bright and photostable fluorescent probes. Given the relatively small size and improved brightness of FDNs, these probes feature potential benefits for both single molecule experiments and general fluorescence imaging,[33-37] including extended observation periods during sample imaging. Thus, the dendritic nanoprobes described herein are a new class of fluorescent probes for biological imaging, supported by the results and applications of FDNs to biological imaging described above.

CITATIONS (1) Selvin, P.; Ha, T. Single-Molecule Techniques: A Laboratory Manual; Cold Spring Harbor Laboratory Pr, 2008.
(2) Betzig, E.; Patterson, G.; Sougrat, R.; Lindwasser, O.; Olenych, S.; Bonifacino, J.; Davidson, M.; Lippincott-Schwartz, J.; Hess, H. Science 2006, 313, 1642.
(3) (a) Hell, S. Science 2007, 316, 1153. (b) Xie et al. Annu. Rev. Biophys., 2008, 37, 417. (c) Huang, B.; Babcock, H.; Zhuang, X. Cell, 2010, 143, 1047. (d) Lord, S. J.; Lee, H. L.; Moerner, W. E. Anal. Chem., 2010, 82, 2192.
(4) (a) Tsien, R. Y. Annu. Rev. Biochem. 1998, 67, 509. (b) Shaner et al. Nat. Biotechnol. 2004, 22, 1567.
(5) Roy, R.; Hohng, S.; Ha, T. Nature Methods 2008, 5, 507.
(6) (a) Bruchez, M.; Moronne, M.; Gin, P.; Weiss, S.; Alivisatos, A. P. Science, 1998, 281, 2013. (b) Chan, W. C. W.; Nie, S.; Science, 1998, 281, 2016.
(7) Benesch, R.; Benesch, R. Science 1953, 118, 447.
(8) Rasnik, I.; McKinney, S.; Ha, T. Nature Methods 2006, 3, 891.
(9) Vogelsang, J.; Kasper, R.; Steinhauer, C.; Person, B.; Heilemann, M.; Sauer, M.; Tinnefeld, P. Angewandte Chemie International Edition 2008, 47, 5465.
(10) (a) Rust, M.; Bates, M.; Zhuang, X. Nature Methods 2006, 3, 793. (b) Huang, B.; Wang, W. Q.; Bates, M.; Zhuang, X. Y. Science 2008, 319, 810. (c) Zhuang, X. Nature Photonics, 2009, 3, 365.
(11) (a) Nirmal et al. M.; Nature, 1996, 383, 802. (b) Wang et al. Nature 2009, 459, 686.
(12) Tomalia, D. A.; Naylor, A.; Goddard, W. A. Angew. Chem. Int. Ed. Engl. 1990, 29, 138.
(13) Tomalia, D. A. Progress in Polymer Science 2005, 30, 294.
(14) Caminade, A.-M.; Hameau, A.; Majoral, J.-P. Chem. Eur. J. 2009, 15, 9270.
(15) Adronov, A.; Frechet, J. M. J. Chem Commun. 2000, 1701.
(16) (a) Wang, S.; Gaylord, B. S.; Bazan, G. C. Adv. Mater. 2004, 16, 2127. (b) Wang, S.; Hong, J. W.; Bazan, G. C. Org. Lett. 2005, 7, 1907.
(17) Liu et al. J. Am. Chem. Soc. 2010, 132, 18054.
(18) Baskin, J. M.; Prescher, J. A.; Laughlin, S. T.; Agard, N. J.; Chang, P. V.; Miller, I. A.; Lo, A.; Codelli, J. A.; Bertozzi, C. R. Proc. Nat. Acad Sci. 2007, 104, 16793.
(19) van Oijen, A. M.; Ketelaars, M.; Kohler, J.; Aartsma, T. J.; Schmidt, J. Science 1999, 285, (5426), 400.
(20) Hofkens et al. J. Am. Chem. Soc. 2000, 122, (38), 9278-9288; Vosch et al. Angewandte Chemie 2001, 113, (24), 4779-4784.
(21) Conley et al. J. Phys. Chem. B 2007, 111, (28), 7929-7931.
(22) Hernando et al. J. Phys. Chem. A 2003, 107, (1), 43-52.
(23) Kasha, M.; Rawls, H.; El-Bayoumi, M. A. Pure Appl. Chem 1965, 11, (3-4), 371-92.
(24) Luchowski et al. Current pharmaceutical biotechnology 2008, 9, (5), 411.
(25) (a) Thompson et al. Biophysical journal 2002, 82, 2775. (b) Yildiz, A.; Forkey, J.; McKinney, S.; Ha, T.; Goldman, Y.; Selvin, P. Science 2003, 300, 2061.
(26) Anthony, S.; Granick, S. Langmuir 2009, 25, 8152.
(27) Steinhauer et al. J. Am. Chem. Soc. 2008, 130, 16840.
(28) Jain et al. Nature 2011, 473, (7348), 484-488.
(29) Adronov et al. J. Am. Chem. Soc. 2000, 122, (6), 1175-1185.

(30) Swallen, S.; Kopelman, R.; Moore, J.; Devadoss, C. *J. Molec. Struc.* 1999, 485, 585-597.
(31) Adronov, A.; Frechet, J. M. *J. Chem. Commun.* 2000, (18), 1701-1710.
(32) Hofkens et al. *J. Am. Chem. Soc.* 2000, 122, (38), 9278-9288.
(33) Huang, B.; Babcock, H.; Zhuang, X. *Cell* 2010, 143, (7), 1047-1058.
(34) Huang, B.; Wang, W.; Bates, M.; Zhuang, X. *Science* 2008, 319, (5864), 810.
(35) Rust, M. J.; Bates, M.; Zhuang, X. *Nature methods* 2006, 3, (10), 793-796.
(36) Zhuang, X. *Nature photonics* 2009, 3, (7), 365.
(37) Steinhauer et al. *J. Am. Chem. Soc.* 2008, 130, (50), 16840-16841.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A dendrimer of Formula I:

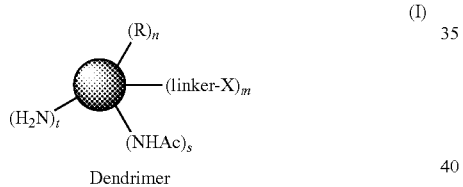

Dendrimer (I)

wherein
the circle of Formula I is a G2-G10 dendrimer;
each R is independently a dye moiety covalently bonded to a branch of the dendrimer;
each linker-X is independently the same or different, wherein linker is S, NH, or O, or a chain of 2-40 atoms that connects a branch of the dendrimer to a group X;
each X is independently R, a reactive group, an affinity label, or a targeting moiety;
n is a value representing about 1% to about 50% of terminal dendrimer groups;
m is a value representing 0% to about 50% of terminal dendrimer groups;
s is a value representing 1% to about 60% of terminal dendrimer groups; and
t is a value representing 0% to about 60% of terminal dendrimer groups;
wherein at least two R groups are different from each other; and wherein the dye moieties of at least two different R groups comprise at least two different Cyanine dyes;
the photobleaching lifetime of the dendrimer is more than 2 times longer than the photobleaching lifetime of a single dye separate from the dendrimer;
the fluorescence emission intensity of the dendrimer is at least two times brighter than a corresponding single dye molecule; and
the diameter of the dendrimer is less than about 20 nm; or a salt thereof.

2. A dendrimer of Formula II:

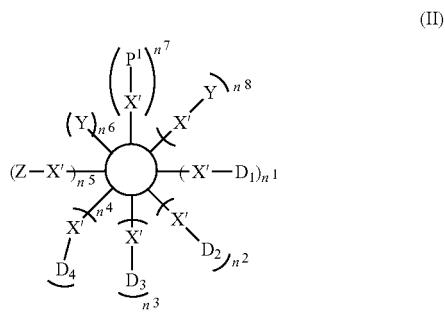

(II)

wherein
$n^1$, $n^2$, $n^3$, $n^4$, $n^5$, $n^6$, $n^7$ and $n^8$ are each independently 0-20, and each of $n^1$, $n^2$, $n^3$, $n^4$, $n^5$, $n^6$, $n^7$ and $n^8$ represents a value corresponding to 0-60% of the terminal groups on the dendrimer surface;
the circle at the core of Formula II represents a dendrimer core having a diameter of about 2 nm to about 10 nm, wherein the dendrimer core comprises a chemically symmetrical or unsymmetrical polymer backbone or hyperbranched polymer backbone;
each X' is independently a linking group selected from —O—, —NH—, —$CO_2$—, —$OCO_2$—, —S—, —P(O)(OR)O—, —NH(CO)—, —NH(CO)O—, —NH(CS)NH—, —$SO_2$—, —$SO_3$—, —$(CH_2)_n$— where n is 1-10, or X' is a direct bond to a nitrogen atom or oxygen atom of the dendrimer core;
each Y and Z is independently —OH, —$NH_2$, —$CO_2H$, —COOR', —SR', —P(O)(OR')$_2$, —OC(O)OR', —NH(CO)OR', —NH(CS)NHR', —$SO_2R'$, or —$SO_3R'$, where R' is an alkali metal, alkaline earth metal, hydrogen, vinyl, ($C_6$-$C_{10}$)aryl, ($C_1$-$C_{12}$)alkyl, or a chemical functional group for bioconjugation, an active carbonate, an active carbamate, a pentafluorophenoxy carbamate, benzylguanine, or O2-benzylcytosine;
$D_1$, $D_2$, $D_3$, and $D_4$ are each independently a dye moiety bonded to a group X; and wherein the dye moiety comprises at least two different Cyanine dyes;
—X'—$P^1$ is —NH—Ac, and at least one —NH—Ac is present;
the photobleaching lifetime of the dendrimer is more than 2 times longer than the photobleaching lifetime of a single dye separate from the dendrimer; and
the fluorescence emission intensity of the dendrimer is at least two times brighter than a corresponding single dye molecule;
or salt thereof.

3. The dendrimer of claim 2 wherein the dendrimer is a poly(amidoamine) (PAMAM) dendrimer.

4. The dendrimer of claim 1 wherein m is not 0% and linker-X comprises one or more ethylene glycol units, one or more ($C_1$-$C_6$)amide units, or a combination thereof.

5. The dendrimer claim 4 wherein X comprises an alkyne, an azide, an N-hydroxysuccinimide (NHS)-ester, a pentafluorophenyl ester, a tetrafluorophenyl ester, a pentafluoroethyl ester, a vinylsulfonyl group, a 2-pyridyldisulfide, a methansufinyldisulfide, a 4-nitrophenylcarbonate group, a 4-nitrophenylcarbamate group, a thiol, an imide group, benzylguanine, or O2-benzylcytosine.

6. The dendrimer claim 5 wherein X comprises biotin or a Ni/Co-NTA group.

7. The dendrimer of claim 6 wherein R comprises a fluorescent dye.

8. The dendrimer of claim 7 wherein R comprises Acridine Orange, Acridine Yellow, an Alexa Fluor dye, an Atto dye, a BODIPY dye, a CF dye antibody conjugate, Cascade Blue, coelenterazine, coumarin, a cyanine dye, dansyl dye, 4',6-diamidino-2-phenylindole (DAPI), erythrosin, FLUO 3, fluorescein, FURA 2, 5-hydroxytryptamine (HAT), a Hoechst dye, INDO 1, JC-1 dye, Lucifer Yellow, Nile Red, Oregon Green dye, propidium iodide, QUIN 2, a rhodamine dye, R-phycoerythrin, R-phycoerythrin-Texas Red, SNARF, or Texas Red.

9. The dendrimer of claim 7 wherein one or more R groups include one or more of Cy2, Cy3, Cy3.5, Cy5, Cy5.5, or Cy7.

10. The dendrimer of claim 1 wherein the molecular diameter of the dendrimer is about 2 nm to about 10 nm.

11. The dendrimer of claim 1 wherein the dendrimer exhibits multiple emission wavelength colors upon excitation to provide a plurality of distinct fluorescent signatures.

12. The dendrimer of claim 1 wherein each of the dye moieties is located within a distance of about 8 nm on the surface of the dendrimer.

13. The dendrimer of claim 12 wherein about 4% to about 15% of the terminal groups of the dendrimer comprise surface bound linker-X groups wherein one or more of the linker-X groups comprises biotin or a Ni/Co-NTA group.

14. A fluorescent probe comprising two or more different dyes conjugated to a dendrimer, and wherein the dyes comprise at least two different Cyanine dyes; wherein at least two of the dyes emit light at different wavelengths upon irradiation, the photobleaching lifetime of the dendrimer is more than 2 times longer than the photobleaching lifetime of a single dye separate from the dendrimer, the fluorescence emission intensity of the probe is at least two times brighter than a corresponding single dye molecule, the dendrimer comprises chains that terminate in N-acetyl groups, and the molecular diameter of the fluorescent probe is less than about 20 nm.

15. A method to provide a distinct spectral fingerprint to a single molecule comprising conjugating a fluorescent probe to a molecule, wherein the fluorescent probe is a dendrimer of claim 1, the fluorescent probe comprises two or more different color dyes conjugated to the dendrimer core moiety of the probe, thereby providing a single molecule with a multiple wavelength emission when irradiated by two or more excitation light sources that correspond to the absorption spectra of the dyes of the probe.

16. A method for labeling a biomolecule comprising:
contacting a sample that includes one or more biomolecules with a plurality of dendrimers of claim 1, wherein a reactive group of the dendrimer conjugates the dendrimer to the biomolecule, thereby allowing detection of one or more of the biomolecules by microscopy.

17. The method of claim 16 wherein the biomolecule is DNA, RNA, a protein, a membrane, or an intracellular component.

18. A method for in vivo targeting and labeling an intracellular component comprising:
contacting one or more intracellular components with a plurality of dendrimers of claim 1, wherein a reactive group of the dendrimer conjugates the dendrimer to one or more of the intracellular components, thereby allowing detection of one or more intracellular component by microscopy.

19. A method of imaging a sample comprising photoswitchable fluorescent probes, the method comprising:
(a) providing a sample labeled with a plurality of photoswitchable fluorescent probes, wherein the photoswitchable fluorescent probes comprise one or more dendrimers of claim 1, at least some of the dye moieties of the photoswitchable fluorescent probes being in a state not capable of emitting light at a first wavelength;
(b) exposing the plurality of photoswitchable fluorescent probes to substantially identical activation light to activate a statistical subset of the photoswitchable fluorescent probes from a state not capable of emitting light at the first wavelength to a state capable of emitting light at the first wavelength;
(c) exciting the activated subset of photoswitchable fluorescent probes with excitation light to cause the activated subset to emit light at the first wavelength;
(d) determining light emitted at the first wavelength by the activated subset of photoswitchable fluorescent probes;
(e) substantially deactivating the activated subset of photoswitchable fluorescent probes;
(f) repeating (b) through (e) one or more times, each time activating a statistically different subset of the plurality of photoswitchable fluorescent probes; and
(g) determining the positions of at least some of the photoswitchable fluorescent probes within the sample by analyzing the light emitted by the activated subsets of the photoswitchable fluorescent probes.

20. The dendrimer of claim 1 wherein the dendrimer is a G5 or G6 poly(amidoamine) (PAMAM) dendrimer.

21. The dendrimer of claim 20 wherein m is a value representing 1% to about 50% of terminal dendrimer groups, and the group X comprises dibenzocyclooctyne (DBCO) conjugated to the dendrimer through a polyethylene glycol chain.

* * * * *